(12) United States Patent
Farina et al.

(10) Patent No.: US 6,787,550 B1
(45) Date of Patent: Sep. 7, 2004

(54) INDOLE DERIVATIVES AND THEIR USE FOR THE TREATMENT OF OSTEOPOROSIS AMONGST OTHER APPLICATIONS

(75) Inventors: Carlo Farina, Milan (IT); Stefania Gagliardi, Milan (IT); Pietro A. Novella, Milan (IT)

(73) Assignee: Nikem Research S.r.l., Milan (IT)

( * ) Notice: Subject to any disclaimer, the term of this patent is extended or adjusted under 35 U.S.C. 154(b) by 0 days.

(21) Appl. No.: 10/018,443

(22) PCT Filed: Jun. 16, 2000

(86) PCT No.: PCT/EP00/05672
§ 371 (c)(1),
(2), (4) Date: Dec. 12, 2001

(87) PCT Pub. No.: WO01/02388
PCT Pub. Date: Jan. 11, 2001

(30) Foreign Application Priority Data

Jun. 18, 1999 (GB) .............................. 9914371

(51) Int. Cl.⁷ ................... C07D 401/12; C07D 403/12; C07D 209/08; A61K 31/404; A61P 9/10
(52) U.S. Cl. ................. 514/254.09; 544/295; 544/373; 546/201; 548/467; 548/506; 548/511; 514/414; 514/323
(58) Field of Search .................. 548/467, 511, 548/506; 514/414, 254.09, 323; 544/295, 373; 546/201

(56) References Cited

FOREIGN PATENT DOCUMENTS

| WO | WO96/21644 | 7/1996 |
|----|------------|--------|
| WO | WO98/01443 | 1/1998 |
| WO | WO99/33822 | 7/1999 |

OTHER PUBLICATIONS

Pezzella et al. (American Journal of Pathology vol. 15, Nov. 1997).*

* cited by examiner

Primary Examiner—Mark L. Berch
Assistant Examiner—Kahsay Habte
(74) Attorney, Agent, or Firm—Wolf, Greenfield & Sacks, P.C.

(57) ABSTRACT

A compound of formula (1)

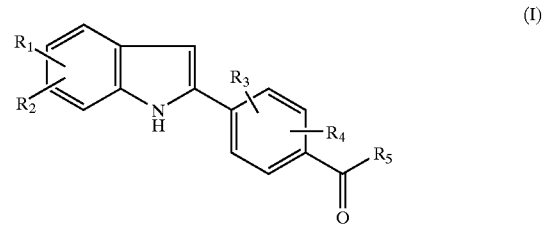

or a salt thereof, or a solvate thereof,
wherein;
$R_1$ and $R_2$ each independently represents $C_{1-6}$alkoxy or halo;
$R_3$ and $R_4$ each independently represents hydrogen, $C_{1-6}$alkoxy, aryl$C_{1-6}$alkoxy, hydroxy, carboxy$C_{1-6}$alkoxy, hydroxy$C_{1-6}$alkoxy, dihydroxy$C_{1-6}$alkoxy, mono- and di-($C_{1-6}$alkyl)amino$C_{1-6}$alkoxy or amino $C_{1-6}$alkoxy, and;
$R_5$ represents —$NR_sR_t$ wherein $R_s$ and $R_t$ each independently represent hydrogen, unsubstituted or substituted $C_{1-6}$alkyl, or unsubstituted or substituted heterocyclyl, a process for the preparation of such a compound, a pharmaceutical composition containing such a compound and the use of the compound or composition in medicine.

22 Claims, No Drawings

INDOLE DERIVATIVES AND THEIR USE FOR THE TREATMENT OF OSTEOPOROSIS AMONGST OTHER APPLICATIONS

This is a 371 of International Application PCT/EP00/05672 filed Jun. 16, 2000, which claims benefit from the following Great Britain Application 9914371.1 filed Jun. 18, 1999.

This invention relates to certain novel compounds, to a process for preparing such compounds, to pharmaceutical compositions containing such compounds and to the use of such compounds and compositions in medicine.

Diseases associated with loss of bone mass are known to be caused by over activity of osteoclast cells. It is also known that certain compounds, usually related to bafilomycin, are useful for treating such diseases. For example, International Application Publication Number WO 91/06296 (Aktiebolaget Astra) discloses certain bafilomycin macrolides for the treatment of bone affecting diseases.

However, bafilomycin derivatives are not selective for osteoclasts in humans. The use of these compounds is therefore associated with unacceptable toxicity due to generalised blockade of other essential v-ATPases. Indeed, to date there is no known treatment which is selective for the human osteoclasts.

The search for a successful treatment for diseases associated with loss of bone mass in humans is further complicated in that the nature of the therapeutic target for the selective inhibition of the osteoclasts is controversial. Thus Baron et al (International Application Publication Number WO 93/01280) indicate that a specific vacuolar ATPase (v-ATPase) has been identified in osteoclasts as a potential therapeutic target. However, the Baron work was carried out in chickens and Hall et al (*Bone and Mineral* 27, 159–166, (1994)), in a study relating to mammals, conclude that in contrast to avian osteoclast v-ATPase, mammalian osteoclast v-ATPase is pharmacologically similar to the v-ATPase in other cells and, therefore, it is unlikely to be a good therapeutic target.

It has now surprisingly been found that particular indole compounds are selective for mammalian osteoclasts, acting to selectively inhibit their bone resorbing activity. These compounds are therefore considered to be particularly useful for the treatment and/or prophylaxis of diseases associated with loss of bone mass, such as osteoporosis and related osteopenic diseases, Paget's disease, hyperparathyroidism and related diseases. These compounds are also considered to possess antitumour activity, antiviral activity (for example against Semliki Forest, Vesicular Stomatitis, Newcastle Disease, Influenza A and B, HIV viruses), antiulcer activity (for example the compounds may be useful for the treatment of chronic gastritis and peptic ulcer induced by *Helicobacter pylori*), immunosupressant activity, antilipidemic activity, antiatheroscierotic activity and to be useful for the treatment of AIDS and Alzheimer's disease. Furthermore, these compounds are also considered useful in inhibiting angiogenesis i.e. the formation of new blood vessels which is observed in various types of pathological conditions (angiogenic diseases) such as rheumatoid arthritis, diabetic retinopathy, psoriasis and solid tumours.

Accordingly, the invention provides a compound of formula (I)

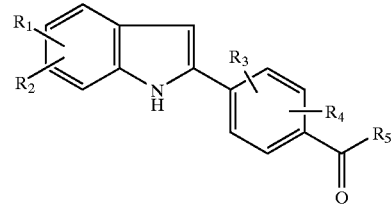

or a salt thereof, or a solvate thereof,
wherein;

$R_1$ and $R_2$ each independently represents $C_{1-6}$alkoxy or halo;

$R_3$ and $R_4$ each independently represents hydrogen, $C_{1-6}$alkoxy, aryl$C_{1-6}$alkoxy, hydroxy, carboxy$C_{1-6}$alkoxy, hydroxy$C_{1-6}$alkoxy, dihydroxy$C_{1-6}$alkoxy, mono-and di-($C_{1-6}$alkyl)amino$C_{1-6}$alkoxy or amino$C_{1-6}$alkoxy, and;

$R_5$ represents —$NR_sR_t$ wherein $R_s$ and $R_t$ each independently represent hydrogen, unsubstituted or substituted $C_{1-6}$alkyl, or unsubstituted or substituted heterocyclyl.

Suitably, $R_1$ and $R_2$ each independently represents methoxy or chloro.

Suitable positions for substitution for $R_1$ or $R_2$ are the 4, 5, 6 or 7 position.

Favourably $R_1$ or $R_2$ are at the 5 or 6 position.

Preferably, $R_1$ is 5-chloro and $R_2$ is 6-chloro.

Suitably, $R_3$ is hydroxy, methoxy, ethoxy, propoxy, benzyloxy, carboxyethoxy, hydroxyethoxy, dihydroxypropoxy, dimethylaminoethoxy or aminopropoxy.

Suitably, $R_3$ is located ortho or meta to the —$COR_5$ moiety.

Suitably, $R_4$ is hydrogen or methoxy.

Suitably, $R_4$ is located meta to the —$COR_5$ moiety.

Suitably, $R_s$ or $R_t$ represent unsubstituted or substituted $C_{1-6}$alkyl, or unsubstituted or substituted heterocyclyl.

When $R_s$ or $R_t$ represent unsubstituted or substituted $C_{1-6}$alkyl, suitable $C_{1-6}$alkyl groups are ethyl, propyl and butyl.

When $R_s$ or $R_t$ represent substituted alkyl, favoured groups are 3-[4(3-methoxyphenyl)piperzin-1-yl]propyl and 3-[4-(2-pyrimidinyl)piperazin-1-yl]propyl.

Suitably, $R_s$ or $R_t$ represent an unsubstituted or substituted piperidinyl group.

Favourably, $R_s$ or $R_t$ represent an unsubstituted or substituted 4-piperidinyl group.

When $R_s$ or $R_t$ represent a substituted piperidinyl group, suitable substituents include $C_{1-6}$alkyl, fused $C_{3-8}$cycloalkyl, aryl$C_{1-6}$alkyl, hydroxy$C_{1-6}$alkyl, polyhydroxy$C_{1-6}$alkyl, $C_{1-6}$alkoxycarbonyl$C_{1-6}$alkyl, carboxy$C_{1-6}$alkyl, and amino$C_{1-6}$alkyl.

Favoured substituents for piperidinyl groups are $C_{1-6}$alcyl groups, especially methyl groups.

When $R_s$ or $R_t$ represent a substituted piperidinyl group, it is preferred that the substituents are attached to one or both of the carbon atoms alpha to the nitrogen atom.

Examples of substituted piperidinyl groups are 1,2,2,6,6-pentamethylpiperidin-4-yl and 2,2,6,6-tetramethylpiperidin-4-yl groups.

Favourably, $R_t$ is hydrogen.

There is a subgroup of compounds falling wholly within formula (I), being of formula (I')

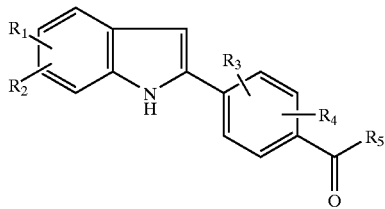

(I')

wherein;

$R_1$, $R_2$, $R_3$, $R_4$, and $R_5$ are as defined in formula (I), with the proviso that formula (I') does not include;

4-(5,6-dichloro-1H-indol-2-yl)-N-(1,2,2,6,6-pentamethylpiperidin-4-yl)benzamide;

4-(5,6-dichloro-1H-indol-2-yl)-3-methoxy-N-(1,2,2,6,6-pentamethylpiperidin-4-yl)benzamide;

4-(5,6-dichloro-1H-indol-2-yl)-2-methoxy-N-(1,2,2,6,6-pentamethylpiperidin-4-yl)benzamide;

4-(5,6-dichloro-1H-indol-2-yl)-3-methoxy-N-(3-diethylaminopropyl)benzamide;

4-(5,6-dichloro-1H-indol-2-yl)-2-methoxy-N-(3-diethylaminopropyl)benzamide;

4-(5,6-dichloro-1H-indol-2-yl)-3-methoxy-N-[3-[4-(3-chlorophenyl)piperazinyl]propyl]benzamide;

4-(5,6-dichloro-1H-indol-2-yl)-2-methoxy-N-[3-[4-(3-chlorophenyl)piperazinyl]propyl]benzamide;

4-(5,6-dichloro-1H-indol-2-yl)-3-methoxy-N-(2,2,6,6-tetramethylpiperidin-4-yl)-N-methylbenzamide, or;

4-(5,6-dichloro-1H-indol-2-yl)-2-methoxy-N-(2,2,6,6-tetramethylpiperidin-4-yl)-N-methylbenzamide.

It is considered that compounds of formula (I') are novel. Accordingly, the present invention provides a compound of formula (I') or a salt thereof or a solvate thereof.

There is a subgroup of compounds falling wholly within formula (I) of formula (IA)

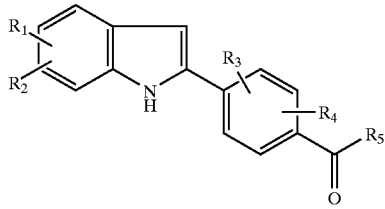

(IA)

wherein;

$R_1$, $R_2$, $R_3$, $R_4$, and $R_5$ are as defined in formula (I), $R_s$ is 3-[4-(3-methoxyphenyl)piperazin-1-yl]propyl or 3-[4-(2-pyrimidinyl)piperazin-1-yl]propyl, and $R_t$ is hydrogen. It is considered that compounds of formula (IA) are novel.

Accordingly, the present invention provides a compound of formula (IA) or a salt thereof or a solvate thereof.

There is a subgroup of compounds falling wholly within formula (I) of formula (IB)

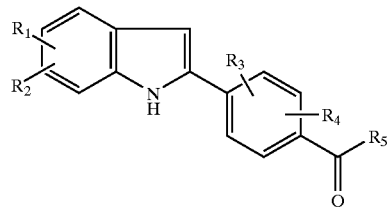

(IB)

wherein;

$R_1$, $R_2$, $R_3$, $R_4$, and $R_5$ are as defined in formula (I), $R_s$ is 3-pyridyl or 3-(6-methoxy)pyridyl, and $R_t$ is hydrogen. It is considered that compounds of formula (IB) are novel.

Accordingly, the present invention provides a compound of formula (IB) or a salt thereof or a solvate thereof.

There is a subgroup of compounds falling wholly within formula (I) of formula (IC)

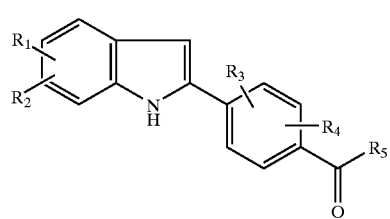

(IC)

wherein;

$R_2$, $R_4$, and $R_5$ are as defined in formula (I), $R_s$ is 2,2,6,6-tetramethylpiperidin-4-yl, $R_t$ is hydrogen, $R_3$ is 3-ethoxy, and $R_1$ is 5-chloro or 5-methoxy. It is considered that compounds of formula (IC) are novel.

Accordingly, the present invention provides a compound of formula (IC) or a salt thereof or a solvate thereof.

There is a subgroup of compounds falling wholly within formula (I) of formula (ID)

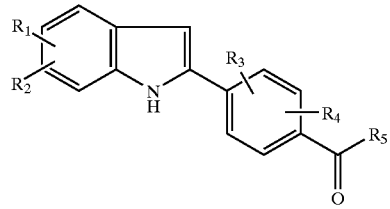

(ID)

wherein;

$R_1$, $R_2$, $R_4$, and $R_5$ are as defined in formula (I), $R_s$ is 2,2,6,6-tetramethylpiperidin-4-yl, $R_t$ is hydrogen, $R_3$ is 2-methoxy, 3-methoxy, 3-ethoxy, 3-propoxy, 3-benzyloxy, 3-(2-carboxyethoxy), 3-(2-hydroxyethoxy), 3-(2,3-dihydroxypropoxy), 3-(2-dimethylaminoethoxy) or 3-(3-aminopropoxy) and 3-hydroxy and $R_4$ is 5-methoxy or hydrogen. It is considered that compounds of formula (ID) are novel.

Accordingly, the present invention provides a compound of formula (ID) or a salt thereof or a solvate thereof.

There is a subgroup of compound falling wholly within formula (I) of formula (IE)

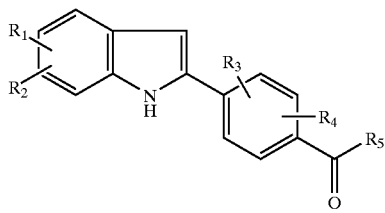

(IE)

wherein;

$R_1$, $R_2$, $R_4$, and $R_5$ are as defined in formula (I), $R_s$ is 1,2,2,6,6-pentamethylpiperidin-4-yl, $R_t$ is hydrogen, and $R_3$ is 2-methoxy or 3-ethoxy, and $R_4$ is 5-methoxy or hydrogen. It is considered that compounds of formula (IE) are novel.

Accordingly, the present invention provides a compound of formula (IE) or a salt thereof or a solvate thereof.

There is a subgroup of compounds falling wholly within formula (I) of formula (IF)

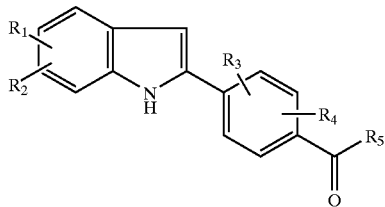

(IF)

wherein;

$R_1$, $R_2$, $R_3$, $R_4$, and $R_5$ are as defined in formula (I), $R_s$ is 1-benzylpiperidin-4-yl, 1-(4-ethoxycarbonyl) butylpiperydin-4-yl, 1-(4-hydroxycarbonyl) butylpiperydin-4-yl and $R_t$ is hydrogen. It is considered that compounds of formula (IF) are novel.

Accordingly, the present invention provides a compound of formula (IF) or a salt thereof or a solvate thereof.

As used herein, the term "alkyl" includes straight or branched chain alkyl groups having from 1 to 12, suitably 1 to 6, preferably 1 to 4, carbon atoms, such as methyl, ethyl, n- and iso-propyl and n- iso-, tert-butyl and pentyl groups, and also includes such alkyl groups when forming part of other groups such as alkoxy or alkanoyl groups.

Suitable substituents for any alkyl groups include heterocyclyl groups, for example piperazinyl.

As used herein, the term "aryl" includes phenyl and naphthyl, especially phenyl.

Suitable optional substituents for any aryl group include up to 5 substituents, suitably up to 3 substituents, selected from alkyl, alkoxy, thioalkyl, hydroxy, halo, aryl, heterocyclyl, trifluoromethyl, alkylcarbonyl, cyano, nitro, or a group —$NR_uR_v$ wherein $R_u$ and $R_v$ each independently represent hydrogen, alkyl or alkylcarbonyl.

Suitable arylalkyl groups include phenylethyl and benzyl groups, especially benzyl. Preferably, substituted aralkyl groups are substituted in the aryl moiety.

As used herein, the terms "heterocyclic" and "heterocyclyl" include saturated or unsaturated single or fused ring heterocyclic groups, each ring having 4 to 11 ring atoms, especially 5 to 8, preferably 5, 6 or 7 which ring atoms include 1, 2 or 3 heteroatoms selected from O, S, or N. Examples of such groups include piperidyl, pyridyl, piperazinyl, and pyrimidinyl.

Suitable optional substituents for any heterocyclyl group includes those mentioned herein with respect to the aryl group.

As used herein, the term "halogen" or "halo" includes fluoro, chloro, bromo and iodo, suitably fluoro and chloro, favourably chloro.

When used herein "acyl" includes alkyl carbonyl.

Certain of the compounds of formula (I) may contain chiral atoms and/or multiple bonds and may therefore exist as stereoisomers. The invention extends to all stereoisomeric forms of the compounds of formula (I) including geometric isomers, diastereoisomers, enantiomers and mixtures thereof, including racemic modifications. Stereoisomers may be separated or resolved by conventional methods or any given isomer may be obtained by conventional stereospecific or asymmetric syntheses.

Suitable salts are pharmaceutically acceptable salts.

Suitable pharmaceutically acceptable salts include acid addition salts and salts of carboxy groups.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

Suitable pharmaceutically acceptable salts of carboxy groups include metal salts, such as for example aluminium, alkali metal salts such as sodium or potassium and lithium, alkaline earth metal salts such as calcium or magnesium and ammonium or substituted ammonium salts, for example those with $C_{1-6}$alkylamines such as triethylamine, hydroxy$C_{1-6}$alkylamines such as 2-hydroxyethylamine, bis(2-hydroxyethyl)amine or tri(2-hydroxyethyl)amine, cycloalkylamines such as dicyclohexylamine, or with procaine, 1,4-dibenzylpiperidine, N-benzyl-b-phenethyl-amine, dehydroabietylamine, N,N'-bisdehydroabietylamine, glucamine, N-methylglucamine, or bases of the pyridine type such as pyridine, collidine, or quinoline.

Suitable solvates of the compounds of the formula (I) are pharmaceutically acceptable solvates, such as hydrates.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

A compound of formula (I) may be prepared by amidation of a suitable carboxylic acid with a suitable amine. Accordingly, the present invention also provides a process for the preparation of a compound of formula (I) or a salt thereof or a solvate thereof, which process comprises the amidation of a compound of formula (II)

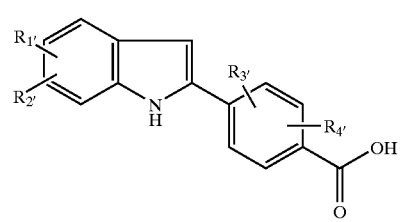

(II)

wherein;

$R_{1'}$, $R_{2'}$, $R_{3'}$, and $R_{4'}$ each respectively represent $R_1$, $R_2$, $R_3$, and $R_4$ as defined in relation to formula (I) or a protected form thereof, with a compound of formula (III)

HNR$_{s'}$R$_{t'}$ (III)

wherein;

R$_{s'}$ and R$_{t'}$ each represent R$_s$ and R$_t$ as defined in relation to formula (I) or a protected form thereof and thereafter, as necessary, carrying out one or more of the following steps:
(i) converting one compound of formula (I) into another compound of formula (I);
(ii) removing any protecting group;
(iii) preparing a salt or a solvate of the compound so formed.

Suitable amidation methods include treating the compound of formula (II) with a compound of formula (III).

The reaction between the compounds of formula (II) and (III) may be carried out under the appropriate conventional amidation conditions, for example in an aprotic solvent such as dimethylformamide, acetonitrile and tetrahydrofuran, at any temperature providing a suitable rate of formation of the required product, conveniently at ambient temperature; preferably the amidation reaction is carried out in the presence of a peptide coupling reagent such as 1-hydroxybenzotriazole (HOBT), and/or 1-(3-dimethylaminopropyl)-3-ethylcarbodiimide hydrochloride (WSC).

A compound of formula (II) may be prepared by cyclising a compound of formula (IV)

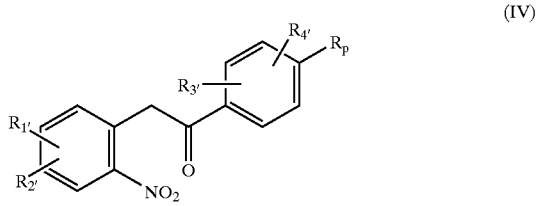

(IV)

wherein;

R$_{1'}$, R$_{2'}$, R$_{3'}$, and R$_{4'}$ are as defined in relation to formula (II) and R$_p$ represents a protected carboxyl group or a group convertible into a carboxyl group and thereafter, as required, converting the group R$_p$ into a carboxyl group.

Suitably, the cyclisation reaction is carried out under reductive cyclisation conditions, for example by using powdered iron/acetic acid mixtures or an alkali metal hydrogensulphite, such as sodium hydrogensulphite, in any suitable solvent such as tetrahydrofuran, ethanol, methanol, or water or mixtures thereof, at any temperature providing a suitable rate of formation of the required product, such as an elevated temperature, conveniently at the reflux temperature of the solvent.

When Rp is a protected carboxyl group, suitable groups include lower alkoxy carbonyl groups, for example methoxy or ethoxy carbonyl groups, which may be removed by conventional hydrolysis methods, for example by use of basic hydrolysis using ethanolic potassium hydroxide.

When Rp is a group convertible into a carboxyl group, suitable groups include cyano group. Such groups may be converted into carboxyl groups using conventional methods for example when R$_p$ is a cyano group it may be converted into a carboxyl group by hydrolysis using conventional methods, for example by use of basic hydrolysis using potassium hydroxide solution in ethanol at reflux.

A preferred value of Rp is a cyano group.

A compound of formula (IV) is prepared by reacting a compound of formula (V)

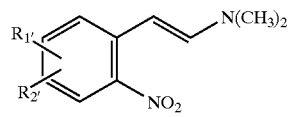

(V)

wherein;

R$_{1'}$ and R$_{2'}$ are as defined in relation to formula (II) with a compound of formula (VI)

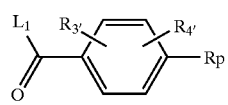

(VI)

wherein;

R$_{3'}$, R$_{4'}$, and Rp are as defined in relation to formula (IV) and L$_1$ represents a leaving group, such as a halogen group, for example a chloro group.

The reaction between the compounds of formula (V) and (VI) may be carried out in an inert hydrocarbon solvent, such as cyclohexane, at any temperature providing a suitable rate of formation of the required product, preferably at an elevated temperature, such as the reflux temperature of the solvent and in presence of a base, preferably a tertiary amine such as triethylamine.

The reaction between the compounds of formulae (V) and (VI) proceeds via an intermediate which is not usually isolated and which provides the required compound of formula (IV) on heating in situ. In an alternative aspect, the intermediate is isolated thereby providing an alternative preparation of the compound of formula (IV) wherein the compound of formula (VII)

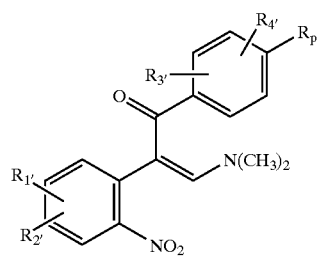

(VII)

wherein;

R$_{1'}$, R$_{2'}$, R$_{3'}$, and R$_{4'}$ are as defined in relation to formula (II) and Rp is as defined in relation to formula (IV), is heated to provide the compound of formula (IV) as hereinbefore defined.

The conversion of compound (VII) into the compound of formula (IV) is conveniently carried out in a polar solvent mixture, such as dioxane and water, usually at the reflux temperature of the solvent mixture in conditions analogous to those described in *J. Het. Chem.* 11, 219–221, (1974).

The compounds of formula (V) are known compounds or they are prepared using methods analogous to those used to prepare known compounds, such as those disclosed by Meervein et al *Ann. Chem.* 641, 1 (1961) and Org. Synth. Collective VII, 34–41.

The compounds of formula (VI) are known, are commercially available, or they are prepared using methods analogous to those used to prepare known compounds, such as those described in *J. March, Advanced Organic Chemistry*, 3rd Edition (1985), Wiley Interscience.

The compounds of formula (III) are known or they are prepared using methods analogous to those used to prepare known compounds, such as those described in J. March, *Advanced Organic Chemistry*, 3rd Edition (1985), Wiley Interscience.

Amines of general formula HNRs'Rt' may be prepared using the methods known in the art for the preparation of amines, for example as taught in *Houben-Weil, Methoden der Organischen Chemie*, Vol. XI/1 (1957) and Vol. E16d/2 (1992), Georg Thieme Verlag, Stuttgart.

Alternatively a compound of formula (II) may be prepared by cyclising a compound of formula (VIII)

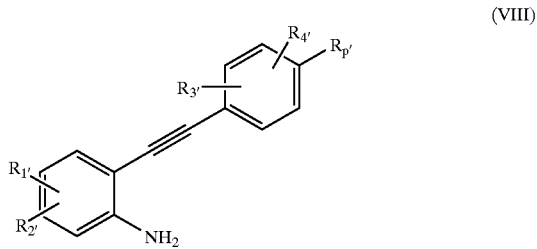

(VIII)

wherein;

$R_{1'}$, $R_{2'}$, $R_{3'}$, and $R_{4'}$ are as defined in relation to formula (II) and $R_{p'}$ represents a protected carboxyl group or a group convertible into a carboxyl group and thereafter, as required, converting the group $R_{p'}$ into a carboxyl group.

Suitably, the cyclisation reaction is carried out using Suzuki reaction conditions, using a palladium catalyst, such as bis(acetonitrile)palladium (II) chloride, in presence of an organic base, such as triethylamine, in any suitable solvent such as tetrahydrofuran thereof at any temperature providing a suitable rate of formation of the required product, preferably at an elevated temperature, such as the reflux temperature of the solvent.

When $R_{p'}$ is a protected carboxyl group, suitable protecting groups include alkyoxy carbonyl groups, for example benzyloxy carbonyl, which may be removed by conventional hydrolysis methods, for example by use of basic hydrolysis using ethanolic potassium hydroxide.

A preferred value of $R_{p'}$ is a benzyloxycarbonyl group.

A compound of formula (VIII) is prepared by reacting a compound of formula (IX)

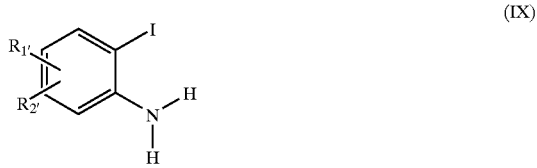

(IX)

wherein;

$R_{1'}$ and $R_{2'}$ are as defined in relation to formula (II) with a compound of formula (X)

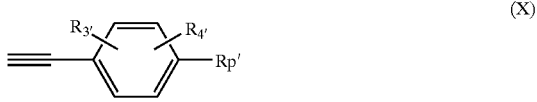

(X)

wherein;

$R_{3'}$, $R_{4'}$ are as defined in relation to formula (II) and $R_{p'}$ is as defined in formula (VIII).

The reaction between the compounds of formula (IX) and (X) may be carried out in an aprotic solvent, such as tetrahydrofuran, at any temperature providing a suitable rate of formation of the required product, preferably from 0–25° C., in presence of a palladium catalyst, preferably bis(triphenylphosphine)palladium (II) chloride, and a copper salt, preferably copper (I) iodide.

The compounds of formula (IX) are known compounds or they are prepared using methods analogous to those used to prepare known compounds, such as those disclosed by Yu M. S. et al *Tetrahedron Letters*, 39, 9347, (1998).

The compounds of formula (X) are prepared by reacting a compound of formula (XI)

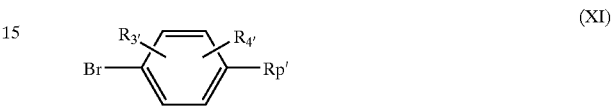

(XI)

wherein;

$R_{3'}$, $R_{4'}$ are as defined in relation to formula (XI) and Rp' is as defined in formula (VIII) with a compound of formula (XII)

≡—SiMe (XII)

The reaction between the compounds of formula (XI) and (XII) may be carried out in an aprotic solvent, such as tetrahydrofuran, at any temperature providing a suitable rate of formation of the required product, preferably from 0–25° C., in presence of a palladium catalyst, preferably bis(triphenylphosphine)palladium (II) chloride, and a copper salt, preferably copper (I) iodide and in presence of a base, preferably a tertiary amine such as triethylamine.

The reaction between the compounds of formulae (XI) and (XII) proceeds via an intermediate which, if desired, is not isolated, and which provides the required compound of formula (X) by removing the protecting silyl group with n-tetrabutylammonium fluoride. In an alternative aspect, the intermediate is isolated thereby providing an alternative preparation of the compound of formula (X) wherein the compound of formula (XIII)

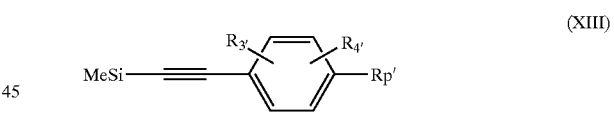

(XIII)

wherein;

$R_{3'}$, and $R_{4'}$ are as defined in relation to formula (II) and Rp' is as defined in relation to formula (VIII) is heated to provide the compound of formula (X) as hereinbefore defined.

The compounds of formula (XI) are known compounds or they are prepared using methods analogous to those used to prepare known compounds, such as those disclosed by Buehler, C. A. et al., *J. Am. Chem. Soc.* 68, 574 (1946).

The compounds of formula (XII) are known, are commercially available, or they are prepared using methods analogous to those used to prepare known compounds, such as those described in *J. March, Advanced Organic Chemistry*, 3rd Edition (1985), Wiley Interscience.

A compound of formula (I) or a salt thereof or a solvate thereof may be isolated from the above mentioned processes according to standard chemical procedures.

The preparation of salts and/or solvates of the compounds of formula (I) may be performed using the appropriate conventional procedure.

If required mixtures of isomers of the compounds of the invention may be separated into individual stereoisomers by conventional means. For example enantiomers may be resolved by the use of an optically active acid as a resolving agent. Suitable optically active acids which may be used as resolving agents are described in "*Topics in Stereochemistry*", Vol. 6, Wiley Interscience, 1971, Allinger, N. L. and Eliel, W. L. Eds.

Alternatively, any enantiomer of a compound of the invention may be obtained by stereospecific synthesis using optically pure starting materials of known configuration.

The absolute configuration of compounds may be determined by conventional methods such as X-ray crystallographic techniques.

The protection of any reactive group may be carried out at any appropriate stage in the aforementioned processes. Suitable protecting groups include those used conventionally in the art for the particular group being protected. Protecting groups may be prepared and removed using the appropriate conventional procedure, for example hydroxy groups, including diols, may be protected as the silylated derivatives by treatment with an appropriate silylating agent such as di-tert-butylsilylbis(trifluoromethanesulphonate). The silyl group may then be removed using conventional procedures such as treatment with hydrogen fluoride, preferably in the form of a pyridine complex and optionally in the presence of alumina, or by treatment with acetyl chloride in methanol. Alternatively benzyloxy groups may be used to protect phenolic groups, the benzyloxy group may be removed using catalytic hydrogenolysis using such catalysts as palladium (II) chloride or 10% palladium on carbon.

Amino groups may be protected using any conventional protecting group, for example tert-butyl esters of carbamic acid may be formed by treating the amino group with di-tert-butyldicarbonate, the amino group being regenerated by hydrolysing the ester under acidic conditions, using for example hydrogen chloride in aqueous ethanol or trifluoroacetic acid in methylene dichloride. An amino group may be protected as a benzyl derivative, prepared from the appropriate amine and a benzyl halide under basic conditions, the benzyl group being removed by catalytic hydrogenolysis, using for example a palladium on carbon catalyst.

Indole NH groups and the like may be protected using any conventional group, for example benzenesulphonyl, methylsulphonyl, tosyl, formyl, acetyl (all of which are removable by treatment with alkaline reagents), benzyl (removable either with sodium in liquid ammonia or with $AlCl_3$ in toluene), allyl (removable by treatment with rhodium (III) chloride under acidic conditions), benzyloxycarbonyl (removable either by catalytic hydrogenation or by alkaline treatment), trifluoroacetyl (removable by either alkaline or acidic treatment), t-butyldimethylsilyl (removable by treatment with tetrabutylammonium fluoride), 2-(trimethylsilyl)ethoxymethyl (SEM) (removable by treatment with tetrabutylammonium fluoride in the presence of ethylendiamine), methoxymethyl (MOM) or methoxyethyl (MEM) groups (removed by mild acidic treatment).

Carboxyl groups may be protected as alkyl esters, for example methyl esters, which esters may be prepared and removed using conventional procedures, one convenient method for converting carbomethoxy to carboxyl is to use aqueous lithium hydroxide.

A leaving group is any group that will, under the reaction conditions, cleave from the starting material, thus promoting reaction at a specified site. Suitable examples of such groups unless otherwise specified are halogen groups, mesyloxy, p-nitrobenzensulphonyloxy and tosyloxy groups.

The salts, esters, amides and solvates of the compounds mentioned herein may as required be produced by methods conventional in the art. For example, acid addition salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR_{s'}R_{t'}$ may be prepared by treating the relevant carboxylic acid with an amine of formula $HNR_{s'}R_{t'}$ wherein $R_{s'}$ and $R_{t'}$ are as defined above. Alternatively, a $C_{1-6}$alkyl ester such as a methyl ester of the acid may be treated with an amine of the above defined formula $HNR_{s'}R_{t'}$ to provide the required amide, optionally in presence of trimethylalluminium following the procedure described in *Tetrahedron Lett.* 48, 4171–4173, (1977).

As mentioned above the compounds of the invention are indicated as having useful therapeutic properties.

Of particular interest is the osteoporosis associated with the peri and post menopausal conditions. Also encompassed are the treatment and prophylaxis of Paget's disease, hypercalcemia associated with bone neoplasms and all the types of osteoporotic diseases as classified below according to their etiology:

Primary Osteoporosis
Involutional
Type I or postmenopausal
Type II or senile
Juvenile
Idiopathic in young adults
Secondary Osteoporosis
Endocrine abnormality
Hyperthyroidism
Hypogonadism
Ovarian agenesis or Turner's syndrome
Hyperadrenocorticism or Cushing's syndrome
Hyperparathyroidism
Bone marrow abnormalities
Multiple myeloma and related disorders
Systemic mastocytosis
Disseminated carcinoma
Gaucher's disease
Connective tissue abnormalities
Osteogenesis imperfecta
Homocystinuria
Ehlers-Danlos syndrome
Marfan's syndrome
Menke's syndrome
Miscellaneous causes
Immobilisation or weightlessness
Sudeck's atrophy
Chronic obstructive pulmonary disease
Chronic alcoholism
Chronic heparin administration
Chronic ingestion of anticonvulsant drugs In addition the invention encompasses the treatment of tumours, especially those related to renal cancer, melanoma, colon cancer, lung cancer and leukemia, viral conditions (for example those involving Semliki Forest virus, Vesicular Stonatitis virus, Newcastle Disease virus, Influenza A and B viruses, HIV virus), ulcers (for example chronic gastritis and peptic ulcer induced by *Helicobacter pylori*), for use as immunosupressant agents in autoimmune diseases and transplantation, antilipidemic agents for the treatment and/or prevention of hypercholesterolemic and atherosclerotic diseases and to be useful for the treatment of AIDS and Alzheimer's disease. These compounds are also considered useful in treating angiogenic diseases, i.e. those pathological conditions which are dependent on angiogenesis, such as rheumatoid arthitis, diabetic retinopathy, psoriasis and solid tumours.

The present invention therefore provides a method for the treatment and/or prophylaxis of diseases associated with over activity of osteoclasts in mammals which method comprises the administration of an effective non-toxic amount of a compound of formula (I), or a pharmaceutically acceptable salt thereof, or a pharmaceutically acceptable solvate thereof.

In a further aspect, the present invention provides a method for the treatment of osteoporosis and related osteopenic diseases in a human or non-human mammal, which comprises administering an effective, non-toxic, amount of a compound of formula (I) or a pharmaceutically acceptable salt thereof or a pharmaceutically acceptable solvate thereof, to a human or non-human mammal in need thereof.

In a further aspect, the present invention also provides a method for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours, in a human or non-human mammal, which comprises administering an effective, non-toxic, amount of a compound of formula (I) or a pharmaceutically acceptable salt thereof or a pharmaceutically acceptable solvate thereof, to a human or non-human mammal in need thereof.

In a still further aspect, the present invention a compound of formula (I) or a pharmaceutically acceptable salt thereof, or a pharmaceutically acceptable solvate thereof, for use as an active therapeutic substance.

In a further aspect, the present invention provides a compound of formula (I) or a pharmaceutically acceptable salt thereof or a pharmaceutically acceptable solvate thereof for use in the treatment or prophylaxis of diseases associated with over activity of osteoclasts in mammals.

In a further aspect, the present invention provides a compound of formula (I) or a pharmaceutically acceptable salt thereof or a pharmaceutically acceptable solvate thereof, for use in the treatment of or prophylaxis of osteoporosis and related osteopenic diseases.

In a further aspect, the present invention provides a compound of formula (I) or a pharmaceutically acceptable salt thereof or a pharmaceutically acceptable solvate thereof for use in the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours, in a human or non-human mammal.

A compound of formula (I), or a pharmaceutically acceptable salt thereof or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I) or a pharmaceutically acceptable salt thereof or a pharmaceutically acceptable solvate thereof and a pharmaceutically acceptable carrier therefor.

Active compounds or a pharmaceutically acceptable salt thereof or a pharmaceutically acceptable solvate thereof are normally administered in unit dosage form.

An amount effective to treat the disorders hereinbefore described depends upon such factors as the efficacy of the active compounds, the particular nature of the pharmaceutically acceptable salt or pharmaceutically acceptable solvate chosen, the nature and severity of the disorders being treated and the weight of the mammal. However, a unit dose will normally contain 0.01 to 50 mg, for example 1 to 25 mg, of the compound of the invention. Unit doses will normally be administered once or more than once a day, for example 1, 2, 3, 4, 5 or 6 times a day, more usually 1 to 3 or 2 to 4 times a day such that the total daily dose is normally in the range, for a 70 kg adult of 0.01 to 250 mg, more usually 1 to 100 mg, for example 5 to 70 mg, that is in the range of approximately 0.0001 to 3.5 mg/kg/day, more usually 0.01 to 1.5 mg/kg/day, for example 0.05 to 0.7 mg/kg/day.

In such treatments the active compound may be administered by any suitable route, e.g. by the oral, parenteral or topical routes. For such use, the compound will normally be employed in the form of a pharmaceutical composition in association with a human or veterinary pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents.

Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the active compound and may be prepared in a conventional manner, for example, as described in the standard textbooks such as 'Dermatological Formulations'—B. W. Barry (Drugs and the Pharmaceutical Sciences—Dekker) or Harrys Cosmeticology (Leonard Hill Books).

Accordingly, the present invention provides the use of a compound of formula (I), or a pharmaceutically acceptable salt thereof, or a pharmaceutically acceptable solvate thereof, for the manufacture of a medicament for the treatment and/or prophylaxis of diseases associated with over activity of osteoclasts in mammals.

In a further aspect, the present invention provides the use of a compound of formula (I), or a pharmaceutically acceptable salt thereof, or a pharmaceutically acceptable solvate thereof, for the manufacture of a medicament for the treatment and/or prophylaxis of osteoporosis and related osteopenic diseases.

In a still further aspect, the present invention provides the use of a compound of formula (I), or a pharmaceutically acceptable salt thereof, or a pharmaceutically acceptable solvate thereof, for the manufacture of a medicament for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours.

No unacceptable toxicological effects are expected with compounds of the invention when administered in accordance with the invention. As is common practice, the compositions will usually be accompanied by written or printed directions for use in the medical treatment concerned.

The following, descriptions, examples and pharmacological methods illustrate the invention but do not limit it in any way.

DESCRIPTIONS AND EXAMPLES

Description 1: trans-4,5-Dichloro-2-nitro-β-dimethylaminostyrene

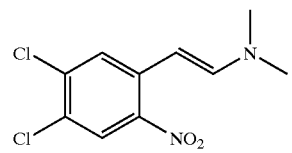

A solution of 10.3 g (50 mmol) of 4,5-dichloro-2-nitrotoluene (*Helv. Chim. Acta* 1936, 19, 434–439) in a mixture of 11.9 g (100 mmol) N,N-dimethylformamide dimethylacetal in DMF (25 ml) was heated at 100° C. for 16 h. The dark reaction mixture was concentrated in vacuo, the residue diluted with methylene chloride and washed twice with water. The organic solution was dried over $MgSO_4$, then concentrated in vacuo affording 12.6 g (48 mmol, yield 96.5%) of the crude title compound as dark red crystals.

Description 2: 2-Methoxy-4-cyanobenzoyl chloride

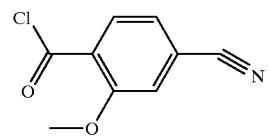

2-Methoxy-4-cyanobenzoic acid (*Tetrahedron Letters*, 1986, 27(49), 5997–6000) (1 g, 5.6 mmol) was dissolved in $CH_2Cl_2$ (20 ml). Oxalyl chloride (1.5 ml, 8.2 mmol) was rapidly introduced into the solution and a drop of DMF was added. A vigorous reaction took place with the abundant evolution of gaseous products. The solution was stirred for 1 h then allowed to stand over night. Solvent was removed using a rotary evaporator to leave 1.1 g of an off white solid (5.6 mmol, yield 99%) that was used without further purification.

Description 3: 3-Methoxy-4-[2-[(4,5-dichloro-2-nitro)phenyl]-1-oxo-ethyl]-benzonitrile

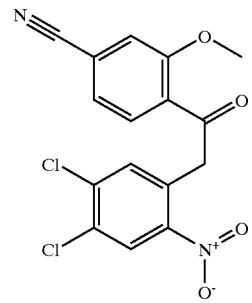

2-Methoxy-4-cyanobenzoyl chloride (1.1 g, 5.6 mmol), prepared as in Description 3, was added portionwise to a stirred solution of trans-4,5-dichloro-2-nitro-β-dimethylaminostyrene (1.47 g, 5.6 mmol) and triethylamine (1.5 ml, 10 mmol) in cyclohexane (20 ml). The solution was then refluxed for 16 h. The reaction was cooled and all the volatile products removed using a rotary evaporator. A dark residue was obtained which was then dissolved in CH$_2$Cl$_2$ (40 ml) and washed once with 10% Na$_2$CO$_3$ solution (20 ml). The organic layer was then dried with anhydrous Na$_2$SO$_4$, filtered and the solvent removed using a rotary evaporator. Dark brown to black powder (2.42 g) was obtained that was dissolved in as little ethyl acetate as possible and hexane was added to this solution to precipitate light brown powder (1.72 g, mp=167–170° C.) that was used without further purification in the next step. This crude intermediate (1.2 g) was dissolved in 1,4-dioxane (20 ml) and water (10 ml) was added. The solution was refluxed for 48 h, filtered while still hot and then chilled in an ice water bath. Yellow to brown crystals were collected on a Buchner funnel obtaining 0.60 g (1.6 mmol, yield 30%) of the title compound, mp=171–174° C.

$^1$H NMR (CDCl$_3$) δ=8.27 (s, 1H); 7.81 (d, 1H); 7.49 (s, 1H); 7.35 (dd, 1H); 7.28 (d, 1H); 4.61 (s, 2H); 4.00 (s, 3H).

Description 4: 3-Methoxy-4-(5,6-dichloro-1H-indol-2-yl)-benzonitrile

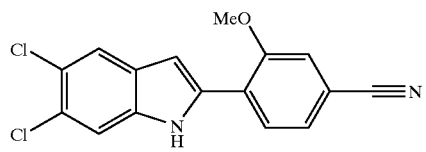

3-Methoxy-4-[2-(4,5-dichloro-2-nitro)phenyl-1-oxo-ethyl]-benzonitrile (0.4 g, 1.0 mmol) was dissolved in EtOH (10 ml) and AcOH (10 ml). The solution was brought gently to reflux and iron powder (0.5 g, 9 mmol) was added in small portions over the period of an hour. The solution was refluxed for 12 h after which the solvents were removed using a rotary evaporator. The residue was extracted several times with THF. After removal of the solvent, crude 3-methoxy-4-(5,6-dichloro-1H-indol-2-yl)benzonitrile (0.35 g, 1.0 mmol, yield 100%) was obtained that was used in the next step without further purification. mp=241–244° C.

$^1$H NMR (DMSO-d$_6$) δ=11.60 (s br, 1H); 7.98 (d, 1H); 7.85 (s, 1H); 7.67 (s, 1H); 7.65 (d, 1H); 7.55 (dd, 1H); 7.14 (s, 1H); 4.00 (s, 3H).

Description 5: 3-Methoxy-4-(5,6-dichloro-1H-indol-2-yl)-benzoic acid

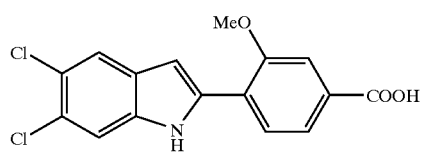

3-Methoxy-4-(5,6-dichloro-1H-indol-2-yl)-benzonitrile (0.35 g, 1.0 mmol) was suspended in 30% NaOH (20 ml) and 95% EtOH (20 ml). The mixture was refluxed for 12 h and then allowed to cool to room temperature. The suspension was concentrated to about half volume using a rotary evaporator and then filtered on a Buchner funnel obtaining a tan to yellow coloured powder. This was stirred for 2 hour in 10% HCl. The solution was then filter to yield 0.256 g (0.76 mmol, yield 69%) of the crude title compound that was purified by chromatography to yield 150 mg of pure title compound, mp>270° C.

$^1$H NMR (DMSO-d$_6$) δ=11.60 (broad s, 1H); 7.92 (d, 1H); 7.83 (s, 1H); 7.66 (m, 3H); 7.10 (s, 1H); 4.02 (s, 3H).

Description 6: 2-Ethoxy-4-aminobenzoic acid

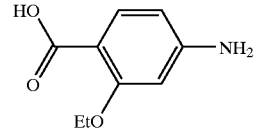

A suspension of methyl 2-ethoxy-4-acetamidobenzoate (50 g, 211 mmol) in aqueous solution of NaOH (15% W/W, 200 ml) was gently refluxed for 16 hours. The resulting pale brown solution was allowed to cool to room temperature and then further cooled in an ice water bath. Concentrated HCl (37% w/w) was added until the solution reached a pH of 6. The solid precipitated from the solution was filtered under vacuum, dried at 50° C. to give 38.3 g of the title compound (yield 100%).

Description 7: 2-Ethoxy-4-cyanobenzoic acid

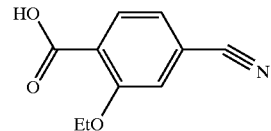

In a 1 l reactor equipped with a sealed mechanical stirrer, CuCN (12 g, 134 mmol) were suspended in 100 ml of distilled water. NaCN (18.3 g, 373 mmol) was added with vigorous stirring and the internal temperature was kept below 40° C. until all the CuCN went into solution. The suspension of 2-ethoxy-4-aminobenzoic acid (20 g, 110 mmol) in water (200 ml) and concentrated HCl (33 ml) was stirred and cooled in an ice bath. When the temperature reached 5° C., a solution of NaNO$_2$ (9.7 g, 140 mmol) in water (30 ml) was added dropwise at such a rate as to maintain the temperature below 5° C. When all the NaNO was added, the solution was slowly introduced through an ice cooled dropping funnel into the reactor containing the NaCN/CuCN solution. A reaction took place with the vigorous formation of N$_2$. A few drops of octanol were added to keep the foaming under control. Stirring was continued for 4 h. The resulting suspension was then extracted with ethyl acetate (3×100 ml) and the organic phase dried over MgSO$_4$ and evaporated under vacuum obtaining 15 g of the title compound (yield 71.1%) as a light brown powder, mp=170–172° C.

Description 8: 3-Ethoxy-4-(5,6-dichloro-1H-indol-2-yl)-benzoic acid

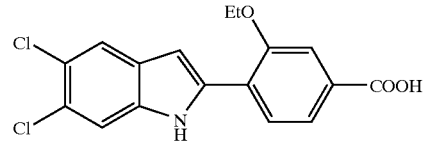

The title compound was prepared starting from 2-ethoxy-4-cyanobenzoic acid, prepared as in Description 7, following the procedure of Description 1–5. The title compound was prepared with an overall yield of 18%, based on the 2-ethoxy-4-cyanobenzoic acid.

$^1$H NMR (DMSO-d$_6$) δ=11.63 (s br, 1H); 7.89 (d, 1H); 7.83 (s, 1H); 7.65 (s, 1H); 7.64 (d, 1H); 7.63 (s, 1H); 7.13 (s br, 1H); 4.27 (q, 2H); 1.48 (t, 3H).

Description 9: Dimethyl 2,5-dimethoxyterephthalate

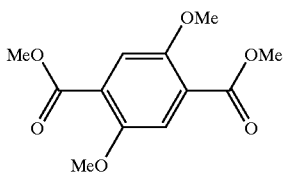

A suspension of 2,5-dihydroxyterephthalic acid (5 g, 25 mmol), K$_2$CO$_3$ (10 g, 72 mmol) and dimethyl sulphate (11 ml, 116 mmol) in acetone (100 ml) was stirred and refluxed for 24 h. The mixture was filtered while still hot and the solvent was evaporated to about half of the original volume. On cooling white needles precipitated and were filtered and dried obtaining 4.6 g of the title compound (yield 73%), mp=141–143° C.

Description 10: 2,5-Dimethoxyterephthalic acid monomethyl ester

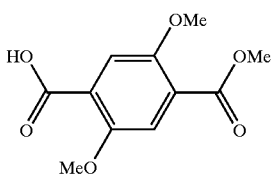

A suspension of dimethyl 2,5-dimethoxyterephthalate (4 g, 15.7 mmol), prepared as in Description 9, in methanolic KOH (0.86 g of KOH in 100 ml MeOH) was refluxed for 3 h. The solution was cooled and the solvent removed under vacuum. The residue was treated with dilute HCl and the solid filtered off. The crude mixture was purified by column chromatogrphy using 1:1 ethyl acetate/hexane as a solvent obtaining 1.72 g of the title compound (yield 44.7%), mp=123–124° C.

Description 11: 2,5-Dimethoxy-4-(5,6-dichloro-1H-indol-2-yl)-benzoic acid

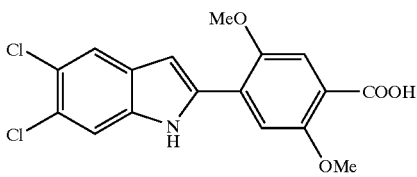

The tide compound was prepared starting from 2,5-dimethoxyterephthalic acid monomethyl ester, prepared as in Description 10, following the procedure of Description 1–5. The tide compound was prepared with an overall yield of 46%, based on 2,5-dimethoxyterephthalic acid monomethyl ester $^1$H NMR (DMSO-d$_6$) δ=11.38 (s br, 1H); 7.79 (s, 1H); 7.68 (s, 1H); 7.51 (s, 1H); 7.43 (s, 1H); 7.11 (d, 1H); 3.92 (s, 3H); 3.91 (s, 3H).

Description 12: 4-Bromo-3-hydroxybenzoic acid

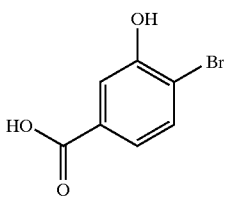

This acid was prepared in similar way to that described by Buehler et al (Buehler, C. A., Harris, J. O., Shacklett, C and Block, B. P.; J. Am. Chem. Soc., 68, 574–577 (1946)). To a stirred suspension of 3-hydroxybenzoic acid (50.0 g, 0.362 mol) in acetic acid (495 ml), at RT under argon, was added a solution of bromine (57.97 g, 0.3627 mol) in acetic acid (192 ml) over 2 h. During the addition the internal temperature rose from 18.0 to 22.0° C. The mixture was stirred for 21 h and then concentrated under vacuum, where approximately (500 ml) of distillate was collected. The resulting concentrated solution was stored at 4° C. for 2 h. The resulting white solid was filtered off and washed with cold water (100 ml). This solid was dissolved in a minimum volume of boiling water (220 ml), filtered and allowed to cool to room temperature. The resulting solid was removed by filtration, washed with cold water and dried in a vacuum oven at 58° C. to give the title compound (12.50 g, yield 15.9%), mp=231–232° C., (lit mp 225–226° C.)[1].

$^1$H NMR (400.13 MHz, DMSO-d$_6$): 13.00 (1H, bs, CO$_2$H), 10.64 (1H, bs, OH), 7.60 (1H, d, H-5, J$_{5-6}$ 8.0 Hz), 7.52 (1H, d, H-2$_1$ J$_{2-6}$ 2.0 Hz), 7.29 (1H, dd, H-6, J$_{2-6}$ 2.0 Hz, J$_{5-6}$ 8.0 Hz)

Description 13: 3-Benzyloxy-4-bromobenzoic acid, benzyl ester

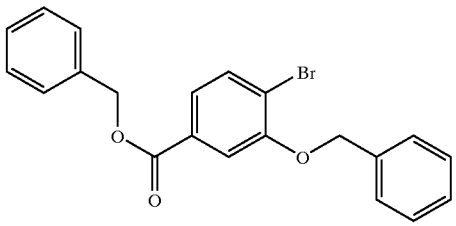

To a stirred suspension of NaH (10.47 g, 60% by wt, 0.2616 mol) in THF (1.40 L), at 13.1° C. under argon, was added a solution of 4-bromo-3-hydroxybenzoic acid (28.11 g, 0.130 mol) in THF (400 ml) over 1.25 h maintaining the internal temperature in the range 4–15° C. After 1.5 h a solution of benzyl bromide (44.3 g, 0.2591 mol) in THF (70 ml) was added over 0.5 h. To the resulting suspension was added DMF (500 ml) and the mixture allowed to warm to room temperature. After a further 15 h extra DMF was added (1.5 L) to the suspension. After approximately 30 minutes the reaction mixture was essentially clear and TLC analysis (25% EtOAc/hexane) indicated that effectively all of the starting material had been consumed. The reaction mixture was quenched with dilute ammonium chloride (100 ml) and concentrated in vacuo. To the concentrate was added ethyl acetate (1.0 L) and dilute ammonium chloride (1.0 L) and the fractions separated. The aqueous fraction was back extracted with ethyl acetate (1×450 ml and 1×300 ml). The total organic fraction was dried over sodium sulphate, filtered and concentrated in vacuo. The resulting solid was crystallised from ethanol:water (9:1; vol:vol, 200 ml), heated at reflux, to which was added ethanol (65 ml) until all the material had dissolved. Water was then added dropwise (17 ml), followed by extra ethanol (8.0 ml). The resulting solution was allowed to slowly cool to ambient temperature. The resulting solid was filtered off and dried (44.54 g). This solid was then dissolved in hot ethanol (227 ml) and water (5.0 ml) added and then allowed to slowly cool to ambient temperature. The resulting crystals were filtered off, washed with cold ethanol (25 ml) and dried in a vacuum oven at 50° C. to give the title compound (36.79 g, yield 71.5%). mp=80.5–81.5° C.

$^1$H NMR (400.13 MHz, CDCl$_3$): 7.67–7.28 (13H, complex m, aromatics), 5.35 (2H, s, CH$_2$Ph), 5.20 (2H, s, CH$_2$Ph).

Description 14: 3-Benzyloxy-4-trimethylsilanylethynyl benzoic acid, benzyl ester

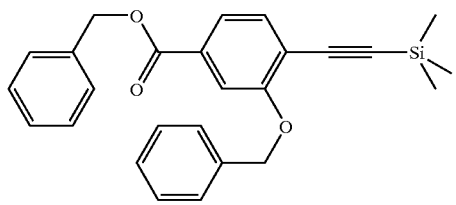

3-Benzyloxy-4-bromobenzoic acid, benzyl ester (33.00 g, 83.07 mmol) was placed in a three necked flask and the atmosphere was replaced, under vacuum, with argon using a Firestone valve. The solid was dissolved in THF (215 ml), with stirring, and then triethylamine (396 ml) was added. The mixture was cooled in an ice/water bath and the solution degassed five times as described above. Copper (I) iodide (127 mg, 0.66 mmol) and bis(triphenylphosphine)palladium (II) chloride (933 mg, 1.33 mmol) were quickly added and the solution degassed twice more. Trimethylsilylacetylene (17.6 ml, 124.6 mmol) was then added dropwise, by syringe, over ten minutes. The cooling bath was then removed and the solution allowed to slowly warm to ambient temperature. After 21 h TLC analysis (25% EtOAc/hexane) indicated that essentially all the starting material had been consumed. The solvents were removed by evaporation in vacuo and ethyl acetate (500 ml) and dilute brine (300 ml) were added. The organic fraction was separated and the aqueous phase was back extracted with ethyl acetate (1×250 ml and 1×100 ml). The total organic fraction was dried over sodium sulphate, filtered and evaporated to give a crude brown solid (36.2 g). The solid was dissolved in hot ethyl acetate (80 ml) where upon the title compound crystallised. This solid was removed by filtration, washed with ethyl acetate and dried in a vacuum oven at 40° C. to give pure title compound (13.75 g, yield 39%), mp=110.5–111.5° C.

$^1$H NMR (400.13M Hz, CDCl$_3$): 7.66–7.28 (13H, complex m, aromatics), 5.36 (2H, s, CH$_2$Ph), 5.19 (2H, s, CH$_2$Ph), 0.26 (9H, s, Si(Me$_3$)$_3$).

The filtrate was loaded on to a silica gel cartridge (400 g, Biotage 75M) which was then eluted with 50% ethyl acetate/hexane, the product fractions were pooled and concentrated in vacuo to give title compound (21.1 g, yield 60%) as a slightly impure light brown solid, which was used without further purification.

Description 15: 3-Benzyloxy-4-ethynylbenzoic acid, benzyl ester

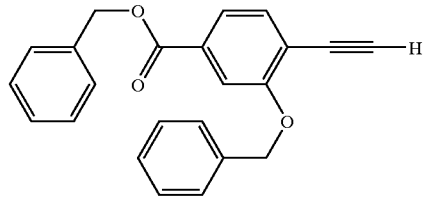

To a stirred solution of 3-benzyloxy-4-trimethylsilanyl-ethynylbenzoic acid, benzyl ester (13.5 g, 32.56 mmol) in THF (182 ml), under argon at −55° C., was added a solution of tetra-n-butylammonium fluoride (33.9 ml, 1.0M in THF) dropwise over 7 minutes. After a further 3 minutes a sample was removed and TLC analysis (25% EtOAc/hexane) indicated that all the starting material had been consumed. The reaction was quenched by the addition of a solution of hydrochloric acid (0.4M, 100 ml) in dilute ammonium chloride. Then ethyl acetate (250 ml) was added and the fractions separated. The aqueous fraction was back extracted with ethyl acetate (1×200 ml and 1×50 ml). The total organic fraction was dried over sodium sulphate, filtered and evaporated to give a brown oil (14.3 g). The oil was taken up in toluene (40 ml) and loaded on to a silica gel cartridge (400 g, Biotage 75M). The cartridge was then eluted as follows: hexane (400 ml), hexane:toluene (1:1, vol:vol, 5.0 L) and finally hexane:toluene (1:1, vol:vol, 2.3 L) containing 4% diethyl ether. The pure fractions were pooled and evaporated in vacuo to give the title compound (7.86 g, yield 70.5%) as a white solid.

$^1$H NMR (400.13 MHz, CDCl$_3$): 7.67–7.27 (13H, complex m, aromatics), 5.34 (2H, s, CH$_2$Ph), 5.22 (2H, s, CH$_2$Ph), 3.44 (1H, s, acetylenic).

Description 16: 4,5-Dichloro-2-iodoaniline

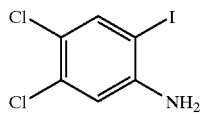

To a stirred solution of 3,4-dichloroaniline (1.944 g, 12.0 mmol) in acetic acid (40 ml) and under argon at ambient temperature was added a solution of iodine monochloride (2.96 g, 18.23 mmol) in acetic acid (25 ml plus 5 ml wash) dropwise over 22 minutes. After stirring for 1.5 h a solid had precipitated which was filtered off and washed with 5% sodium thiosulphate (100 ml). The solid was dissolved in ethyl acetate (100 ml) and washed with saturated sodium carbonate (100 ml) and water (100 ml). The resulting solid was dried over sodium sulphate, filtered and evaporated to give a dark coloured solid (2.69 g). The crude solid was dissolved in EtOAc/hexane (1:1, vol:vol, 6.0 ml) and loaded on a to a silica cartridge (90 g, Biotage) which was eluted as follows: hexane (600 ml), 4% EtOAc in hexane (1 L) and 5% EtOAc in hexane (1 L). The pure fractions were concentrated in vacuo to give the title compound as an off white solid (0.912 g, yield 26.4%).

$^1$H NMR (400.13 MHz, CDCl$_3$): 7.66 (1H, s, H-3), 6.81 (1H, s, H-6), 4.14 (2H, bs, —NH$_2$). MS (AP$^+$): m/z 288.0 and 290.1 (MH$^+$).

Description 17: 4-(2-Amino-4,5-dichloro-phenylethynyl)-3-benzyloxybenzoic acid, benzyl ester

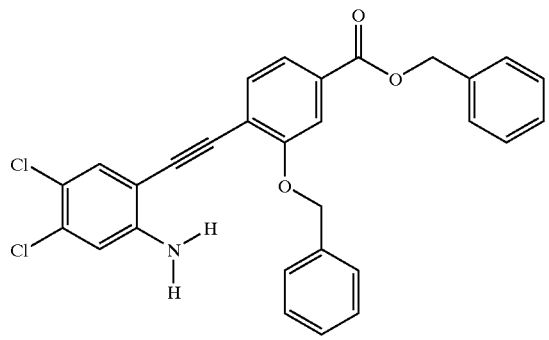

3-Benzyloxy-4-ethynylbenzoic acid, benzyl ester (820 mg, 2.395 mmol) and 4,5-dichloro-2-iodoaniline (710 mg, 2.467 mmol) were placed in a three necked flask and the atmosphere was replaced, under vacuum, with argon using a Firestone valve. The solids were then dissolved in THF (13.0 ml), with stirring, and then triethylamine (20 ml) was added. The mixture was cooled in an ice/water bath and the solution degassed four times as described above. Copper (I) iodide (4 mg, 0.02 mmol) and bis(triphenylphosphine)palladium (II) chloride (27 mg, 0.04 mmol) were quickly added and the solution degassed twice more. The cooling bath was then removed and the solution allowed to slowly warm to ambient temperature. After stirring for 6 h at ambient temperature, TC analysis (25% EtOAc/hexane) indicated that all the starting 3-benzyloxy-4-ethynylbenzoic acid, benzyl ester had been consumed. The solvents were removed by evaporation in vacuo and ethyl acetate (50 ml) and dilute sodium hydrogen carbonate (25 ml) were added. The organic fraction was separated and the aqueous phase was back extracted with ethyl acetate (1×25 ml). The total organic fraction was dried over sodium sulphate, filtered and evaporated to give a pale yellow solid (1.28 g). This solid was dissolved in chloroform (50 ml), silica gel added (Merck 9385, 3.25 g) and the mixture concentrated in vacuo. The crude material, preloaded on silica, was purified by chromatography (Biotage 40 g). The cartridge was eluted with chloroform:hexane (70:30), the pure fractions were pooled and concentrated in vacuo to give the title compound (1.113 g, yield 92.5%) as a pale yellow solid. A sample was recrystallised from toluene:chloroform (45:55), mp=152.5–153.5° C.
$^1$H NMR (400.13 MHz, CDCl$_3$): 7.71 (2H, m, aromatic), 7.57–7.20 (12H, complex m, aromatics), 6.63 (1H, s, aromatic), 5.38 (2H, s, CH$_2$Ph), 5.15 (2H, s, CH$_2$Ph), 3.94 (2H, s, —NH$_2$). MS (AP$^+$): m/z 502.2 and 502.4 (MH$^+$).

Description 18: 3-Benzyloxy-4-(5,6-dicholoro-1H-indol-2-yl)benzoic acid, benzyl ester

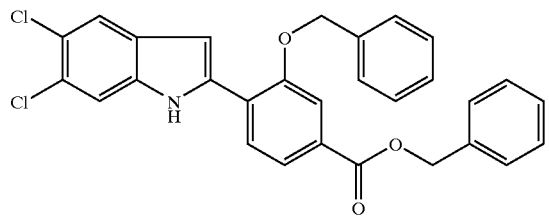

4-(2-Amino-4,5-dichloro-phenylethynyl)-3-benzyloxybenzoic acid, benzyl ester (28.32 g, 56.38 mmol) was dissolved in warm acetonitrile (1.50 L), with stirring under argon. The mixture was cooled in an ice/water bath and the solution degassed on low vacuum, using a Firestone valve, with the atmosphere being replaced with argon. This procedure was repeated five times. The stirred mixture was warmed to 66° C. and bis(acetonitrile)palladium(II) chloride (1.666 g, 5.638 mmol) quickly added and then warmed to 75° C. After 1.5 h a sample was removed and analysed by TLC (25% EtOAc/hexane), which indicated that all the starting material had been consumed. The reaction was allowed to slowly cool to ambient temperature, whereupon the title compound crystallised out of solution. The solid was removed by filtration, washed with cold acetonitrile (125 ml) and dried in a vacuum oven to give the title compound (21.375 g, yield 75.5%) as a white solid, mp=168–169° C.
$^1$H NMR (400.13 MHz, CDCl$_3$): 9.79 (1H, bs, —NH), 7.90–7.76 (3H, complex m, aromatics), 7.68 (1H, s, aromatic), 7.55–7.32 (10H, complex m, aromatics), 7.22 (1H, s, aromatic), 6.91 (1H, m, aromatic), 5.39 (2H, s, CH$_2$Ph), 5.29 (2H, s, CH$_2$Ph). MS (AP$^+$): m/z 502.2 and 502.4 (MH$^+$).

Description 19: 3-Benzyloxy-4-(5,6-dicholoro-1H-indol-2-yl)benzoic acid

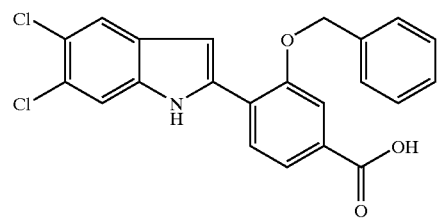

A solution of 3-benzyloxy-4-(5,6-dicholoro-1H-indol-2-yl)benzoic acid, benzyl ester (0.2 g, 0.398 mmol) in EtOH (10 ml) and THF (5 ml) with NaOH (5.3 mg, 1.33 mmol) was refluxed for 3 h. After cooling the solvent was removed under vacuum and the residue treated with 37% HCl. The precipitate was filtered, washed with water and dried under vacuum to give 0.14 g (yield 85%) of the title compound as a yellow powder, mp=>250° C.

Example 1

4-(5,6-Dichloro-1H-indol-2-yl)-3-ethoxy-N-(2,2,6,6-tetramethylpiperidin-4-yl)-benzamide

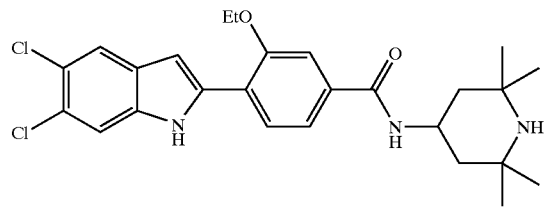

To a suspension of 3-ethoxy-4-(5,6-dichloro-1H-indol-2-yl)-benzoic acid (200 mg, 0.57 mmol), prepared as in Description 8, in CH$_3$CN (14 ml) and THF (6 ml), WSC (N-(3-Dimethylaminopropyl)-N'-ethylcarbodiimide hydrochloride) (104 mg, 55 mmol) and 1-hydroxybenzotriazole (77 mg, 0.57 mmol) were added and the reaction was refluxed for 3 h.
4-Amino-2,2,6,6-tetramethylpiperidine (108 mg, 0.7 mmol) were introduced into the reaction mixture and refluxing continued for another 2 h. The reaction was cooled and the solvent was removed under vacuum. The residue was treated with 30 ml of 10% NaOH solution and then filtered. The resulting solid was washed with water, dried and purified by chromatography on silica gel to yield 154 mg of the title compound as light yellow powder (yield 55%), mp=253–255° C.

$^1$H NMR (DMSO-$d_6$) δ=11.56 (s br, 1H); 8.28 (d br, 1H); 7.85 (d, 1H); 7.82 (s, 1H) 7.64 (s, 1H); 7.59 (s, 1H); 7.57 (d, 1H); 7.11 (s, 1H); 4.40–4.21 (m, 1H); 4.30 (q, 2H); 1.80 (d br, 2H); 1.50 (t, 3H); 1.30 (m, 2H); 1.28 (s, 6H); 1.15 (s, 6H).

ESI POS; AQA; solvent: MeOH/spray 3 kV/skimmer: 20 V/probe 135° C.: m/z 488 (MH$^+$)

Example 2

4-(5,6-Dichloro-1H-indol-2-yl)-3-benzyloxy-N-(2,2,6,6-tetramethylpiperidin-4-yl)-benzamide

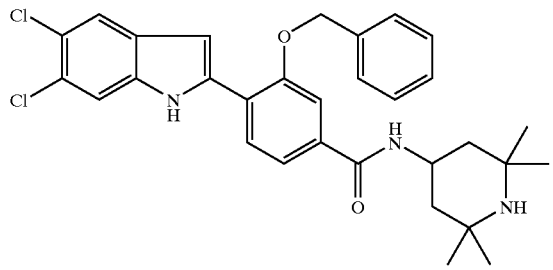

To a solution of 3-benzyloxy-4-(5,6-dichloro-1H-indol-2-yl) benzoic acid (0.14 g, 0.34 mmol), prepared as in Description 19, in THF (14 ml), WSC (N-(3-Dimethylaminopropyl)-N'-ethylcarbodiimide hydrochloride) (0.078 g, 0.408 mmol) and 1-hydroxybenzotriazole (0.0551 g, 0.408 mmol) was refluxed for 6 h. A solution of 4-amino-2,2,6,6-tetramethylpiperidine (0.064 g, 0.408 mmol) in THF (2 ml) was added dropwise and refluxed for additional 2 h. The solvent was removed under vacuum and the residue suspended in water. The solid was filtrated and dried under vacuum. The solid was triturated with CH3CN (5 ml) to give 0.094 g (yield 45%) of the title compound as a white powder, mp=220° C.

$^1$H-NMR (DMSO-$d_6$) δ=11.64 (s br, 1H); 8.24 (d br, 1H); 7.87 (d, 1H); 7.76 (s, 1H); 7.68 (d, 1H); 7.62 (s, 1H); 7.59 (dd, 1H); 7.52 (d, 2H); 7.42 (dd, 2H); 7.34 (dd, 1H); 7.06 (d, 1H); 5.40 (s, 2H); 4.38–4.23 (m, 1H); 1.76 (dd, 2H); 1.25 (dd, 2H); 1.23 (s, 6H); 1.12 (s, 6H).

ESI POS; AQA; solvent: MeOH/spray 3 kV/skimmer: 20 V/probe 135° C.: m/z 550 (MH$^+$)

Example 3

4-(5,6-Dichloro-1H-indol-2-yl)-3-hydroxy-N-(2,2,6,6-tetramethylpiperidin-4-yl)-benzamide

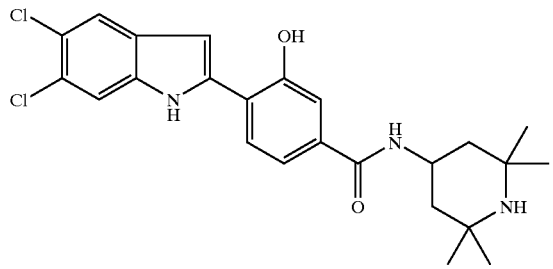

A mixture of 4-(5,6-dichloro-1H-indol-2-yl)-3-benzyloxy-N-(2,2,6,6-tetramethylpiperidin-4-yl)-benzamide (0.08 g, 0.145 mmol), prepared as described in Example 2, in 37% HCl (5 ml) and EtOH (5 ml) was refluxed for 3 h. After cooling the solvent was removed under vacuum. The resulting solid was purified by column chromatography over silica gel (CH$_2$Cl$_2$/MeOH/NH$_4$OH 86:10:0.6) to yield, after trituration with CH$_3$CN, 0.02 g (yield 39%) of the title compound as a white solid, mp>270° C.

$^1$H-NMR (DMSO-$d_6$) δ=11.44 (s br, 1H); 8.16 (d br, 1H); 7.80 (d, 1H); 7.78 (s, 1H); 7.69 (s, 1H); 7.48 (d, 1H); 7.39 (dd, 1H); 7.08 (s, 1H); 4.36–4.20 (m, 1H); 1.73 (dd, 2H); 1.23 (dd, 2H); 1.23 (s, 6H); 1.11 (s, 6H).

ESI POS; AQA; solvent: MeOH/spray 3 kV/skimmer: 20 V/probe 135° C.: m/z 460 (MH$^+$)

Example 4

4-(5,6-Dichloro-1H-indol-2-yl)-3-propoxy-N-(2,2,6,6-tetramethylpiperidin-4-yl)benzamide

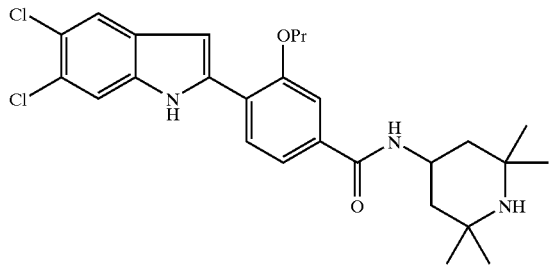

A mixture of 4-(5,6-dichloro-1H-indol-2-yl)-3-hydroxy-N-2,2,6,6-tetramethylpiperidin-4-yl)benzamide (0.05 g, 0.109 mmol), prepared as described in Example 3, K$_2$CO$_3$ (0.045 g, 0.33 mmol) and 2-bromo-propane (0.046 mg, 0.33 mmol) in aceton (5 ml) was refluxed for 8 h. After cooling the mixture was filtered and the organic phase was removed under vacuum, the residue was chromatographed over silica gel with CH$_2$Cl$_2$/MeOH/NH$_4$OH 32% (86:10:0.6). The compound obtained was triturated with iPr$_2$O and filtered to obtain 0.017 mg (yield 37%) of the title compound as a white powder, mp>250° C.

$^1$H-NMR (DMSO-$d_6$) δ=11.55 (s br, 1H); 8.19 (d br, 1H); 7.84 (d, 1H); 7.83 (s, 1H); 7.62 (s, 1H); 7.58 (s, 1H)7.56 (dd, 1H); 7.10 (d, 1H); 4.37–4.24 (m, 1H); 4.18 (t, 2H); 1.96–1.84 (m, 2H); 1.73 (dd, 2H); 1.20 (dd, 2H); 1.20 (s, 6H); 1.08 (s, 6H); 1.05 (t, 3H).

ESI POS; AQA; solvent: MeOH/spray 3 kV/skimmer: 20 V/probe 135° C.: m/z 502 (MH+).

TABLE 1

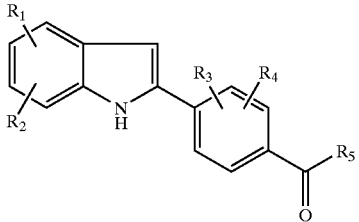

| Ex. | Name | R₁ | R₂ | R₃ | R₄ | R₅ |
|---|---|---|---|---|---|---|
| 5 | 4-(5,6-Dichloro-1H-indol-2-yl)-N-[3-[4-(3-methoxy-phenyl)piperazin-1-yl]propyl]-3-methoxybenzamide | 5-Cl | 6-Cl | 3-OMe | —H | -NH-CH₂CH₂CH₂-N(piperazine)N-(3-methoxyphenyl) |
| 6 | 4-(5,6-Dichloro-1H-indol-2-yl)-N-[3-[4-(2-pyrimidyl)piperazin-1-yl]propyl]-3-methoxy-benzamide | 5-Cl | 6-Cl | 3-OMe | —H | -NH-CH₂CH₂CH₂-N(piperazine)N-(2-pyrimidyl) |
| 7 | 4-(5,6-Dichloro-1H-indol-2-yl)-N-(2,2,6,6-tetra-methylpiperidin-4-yl)-3-methoxybenzamide | 5-Cl | 6-Cl | 3-OMe | —H | -NH-(2,2,6,6-tetramethylpiperidin-4-yl) |
| 8 | 4-(5,6-Dichloro-1H-indol-2-yl)-N-(1,2,2,6,6-penta-methylpiperidin-4-yl)-3-ethoxybenzamide | 5-Cl | 6-Cl | 3-OEt | —H | -NH-(1,2,2,6,6-pentamethylpiperidin-4-yl) |
| 9 | 4-(5,6-Dichloro-1H-indol-2-yl)-N-(3-pyridyl)-3-ethoxybenzamide | 5-Cl | 6-Cl | 3-OEt | —H | -NH-(3-pyridyl) |
| 10 | 4-(5,6-Dichloro-1H-indol-2-yl)-N-(3-(6-methoxy-pyridyl))-3-ethoxybenzamide | 5-Cl | 6-Cl | 3-OEt | —H | -NH-(6-methoxypyridin-3-yl) |
| 11 | 4-(5,6-Dichloro-1H-indol-2-yl)-N-(1-benzyl-piperidin-4-yl)-3-ethoxybenzamidehydrochloride | 5-Cl | 6-Cl | 3-OEt | —H | -NH-(1-benzylpiperidin-4-yl) |
| 12 | 4-(5,6-Dichloro-1H-indol-2-yl)-N-(2,2,6,6-tetra-methylpiperidin-4-yl)-2,5-dimethoxybenzamide | 5-Cl | 6-Cl | 2-OMe | 5-OMe | -NH-(2,2,6,6-tetramethylpiperidin-4-yl) |

TABLE 1-continued

| | | | | | | |
|---|---|---|---|---|---|---|
| 13 | 4-(5,6-Dichloro-1H-indol-2-yl)-N-(1,2,2,6,6-penta-methylpiperidin-4-yl)-2,5-dimethoxybenzamide | 5-Cl | 6-Cl | 2-OMe | 5-OMe | (N-methyl-1,2,2,6,6-pentamethylpiperidin-4-yl)amino |
| 14 | 4-(5-Methoxy-6-chloro-1H-indol-2-yl)-N-(2,2,6,6-tetramethylpiperidin-4-yl)-3-ethoxybenzamide | 5-OMe | 6-Cl | 3-OEt | —H | (N-methyl-2,2,6,6-tetramethylpiperidin-4-yl)amino |
| 15 | 4-(5,6-Dichloro-1H-indol-2-yl)-3-methoxy-N-((1-ethoxycarbonylbutyl)piperidin-4-yl)benzamide | 5-Cl | 6-Cl | 3-OMe | —H | (N-methyl-1-(4-ethoxycarbonylbutyl)piperidin-4-yl)amino |
| 16 | 4-(5,6-Dichloro-1H-indol-2-yl)-3-methoxy-N-((carboxybutyl)piperidin-4-yl)benzamide | 5-Cl | 6-Cl | 3-OMe | —H | (N-methyl-1-(4-carboxybutyl)piperidin-4-yl)amino |

| Ex. | MS | MP °C. | N.M.R. |
|---|---|---|---|
| 5 | A) ESI POS; TSQ 700; solvent: MeOH/spray 4.5 kV/skimmer: 60 V/capillary 220° C.: m/z 474 (MH+)<br>B) CID Offset = −56 V: m/z 567; 375; 318. | 201–205 | $^1$H-NMR(DMSO-d$_6$) δ = 11.53(s br, 1H); 8.55(t br, 1H); 7.88(d, 1H); 7.81(s, 1H); 7.66(s, 1H); 7.60(d, 1H); 7.57(dd, 1H); 7.10(dd, 1H); 7.04(m, 1H); 6.51(dd, 1H); 6.43(dd, 1H); 6.35(dd, 1H); 4.00(s, 3H); 3.70(s, 3H); 3.30(m, 2H); 3.13(m, 4H); 2.58(m, 4H); 2.41(t, 2H); 1.80–1.72(m, 2H). |
| 6 | A) ESI POS; TSQ 700; solvent: MeOH/spray 4.5 kV/skimmer: 60 V/capillary 220° C.: m/z 539 (MH+)<br>B) CID Offset = −56 V: m/z 539; 575; 318. | 234–237 | $^1$H-NMR(DMSO-d$_6$ at 343 K.) δ = 11.30(s br, 1H); 8.32(d, 2H); 8.31(t br, 1H); 7.85(d, 1H); 7.79(s, 1H); 7.68(s, 1H); 7.60(s br, 1H); 7.56(d, 1H); 7.01(s br, 1H); 6.59(t, 1H); 4.02(s, 3H); 3.77 (m, 4H); 3.40(dt, 2H); 2.50–2.40(m, 6H); 1.87–1.73(m, 2H). |
| 7 | A) ESI POS; TSQ 700; solvent: MeOH/spray 4.5 kV/skimmer: 60 V/capillary 220° C.: m/z 474 (MH+)<br>B) CID Offset = −56 V: m/z 474; 457; 401; 318; 290; 123; 58. | 151–156 | $^1$H-NMR(DMSO-d$_6$) δ = 11.30(s br, 1H); 7.95(d br, 1H); 7.82(d, 1H); 7.77(s, 1H); 7.68(s, 1H); 7.61(d, 1H); 7.56(dd, 1H); 7.01(d, 1H); 4.45–4.30(m, 1H); 4.01(s, 3H); 1.80(m, 2H); 1.30(m, 2H); 1.30(s, 6H); 1.15(s, 6H). |
| 8 | ESI POS; AQA; solvent: MeOH/spray 3 kV/skimmer: 20 V/probe 135° C.: m/z 502 (MH+) | >250 | $^1$H-NMR(DMSO-d$_6$) δ = 11.55(s br, 1H); 8.22(d br, 1H); 7.85(d, 1H); 7.82(s, 1H); 7.63(s, 1H); 7.58(s, 1H); 7.57(d, 1H); 7.10(br, 1H); 4.29(q, 2H); 4.29–4.14(m, 1H); 2.22(s, 3H); 1.75(dd, 2H); 1.50(t, 2H); 1.49(t, 3H); 1.12(s, 6H); 1.08(s, 6H). |
| 9 | EI; TSQ 700; 180° C.: 70 V; 200 uA: m/z 425 (M+.); 332; 304; 212. | 237–239 | $^1$H-NMR(DMSO-d$_6$) δ = 11.60(s br, 1H); 10.49(s, 1H); 8.95(d, 1H); 8.33(dd, 1H); 8.20(ddd, 1H); 7.95(d, 1H); 7.84(s, 1H); 7.72(d, 1H); 7.70(s, 1H); 7.66(s, 1H); 7.41(dd, 1H); 7.18(d, 1H); 4.35(q, 2H); 1.50(t, 3H). |
| 10 | EI; TSQ 700; 180° C.: 70 V; 200 uA: m/z 455 (M+.); 332; 304. | 258–260 | $^1$H-NMR(DMSO-d$_6$) δ = 11.60(s br, 1H); 10.30(s, 1H); 8.52(d, 1H); 8.05(dd, 1H); 7.94(d, 1H); 7.83(s, 1H); 7.70(d, 1H); 7.69(s, 1H); 7.65(s, 1H); 7.15(s, 1H); 6.86(d, 1H); 4.34(q, 2H); 3.87(s, 3H); 1.50(t, 3H). |
| 11 | EI; TSQ 700; 180° C.: 70 V: 200 uA: m/z 521 (M+.); 350; 332; 212; 173; 132; 91; 82. | 295 | $^1$H-NMR(DMSO-d$_6$) δ = 11.65(s br, 1H); 8.30(d br, 1H); 7.86(d, 1H); 7.81(s, 1H); 7.65(s, 1H); 7.58(s, 1H); 7.56(d, 1H); 7.36–7.21(m, 5H); 7.10(s, 1H); 4.29(q, 2H); 3.89–3.72(s, 1H); 3.49(s, 2H); 2.83(d br, 2H); 2.02(dd br, 2H); 1.80(m, 2H); 1.61(dq, 2H); 1.49(t, 3H). |
| 12 | A) EI; TSQ 700; 400 mA; 70 V: m/z 567 (MH+)<br>B) ESI POS; AQA; solvent: MeOH/spray 3 kV/skimmer: 20 V/probe 135° C.: m/z 504 (MH+) | 148–152 | $^1$H-NMR(DMSO-d$_6$) δ = 11.60(s br, 1H); 7.95(d br, 1H); 7.82(s, 1H); 7.69(s, 1H); 7.52(s, 2H); 7.13(s br, 1H); 4.40–4.21(m, 1H); 4.00(s, 3H); 3.92(s, 3H); 1.78(dd, 2H); 1.20(s, 6H); 1.12(dd, 2H); 1.06(s, 6H). |
| 13 | A) ESI POS; TSQ 700; solvent: MeOH/spray 4.5 kV/skimmer: 60 V/capillary 220° C.: m/z 518 (MH+)<br>B) ESI DAU +518 (Collision gas: Argon): m/z 518; 487; 431; 365; 348; 123. | 143–147 | $^1$H-NMR(DMSO-d$_6$) δ = 11.58(s br, 1H); 7.95(d br, 1H); 7.81(s, 1H); 7.68(s, 1H); 7.51(s, 2H); 7.13(s br, 1H); 4.28–4.10(m, 1H); 3.95(s, 3H); 3.90(s, 3H); 2.20(s, 3H); 1.78(dd, 2H); 1.39(dd, 2H); 1.10(s, 6H); 1.06(s, 6H). |
| 14 | ESI POS; AQA; solvent: MeOH/spray 3 kV/skimmer: 20 V/probe 135° C.: m/z 484 (MH+). | 231–232 | $^1$H-NMR(DMSO-d$_6$) δ = 11.18(d br, 1H); 8.18(d, 1H); 7.83(d, 1H); 7.56(d, 1H); 7.55(d, 1H); 7.46(d, 1H); 7.24(s, 1H); 7.07(d, 1H); 4.38–4.25(m, 1H); 4.27(q, 2H); 3.85(s, 3H); 1.73(dd, 2H); 1.50(t, 3H); 1.20(dd, 2H); 1.20(s, 6H); 1.08(s, 6H). |

TABLE 1-continued

| | | | |
|---|---|---|---|
| 15 | ESI POS; AQA; solvent: MeOH/ spray 3 kV/skimmer: 20 V/probe 135° C.: m/z 546 (MH+). | 188–190 | $^1$H-NMR(DMSO-d$_6$) δ = 11.53(s br, 1H); 8.27(d, 1H); 7.87(d, 1H); 7.81(s, 1H); 7.66(s, 1H); 7.59(s, 1H); 7.57(d, 1H); 7.06(d, 1H); 4.06(q, 2H); 4.02(s, 3H); 3.86–3.70(m, 1H); 2.86(d br, 2H); 2.33–2.25(m, 4H); 1.94(dd, 2H); 1.81(dd, 2H); 1.66–1.38(m, 6H); 1.19(t, 3H). |
| 16 | ESI POS; AQA; solvent: MeOH/ spray 3 kV/skimmer: 20 V/probe 135° C.: m/z 518 (MH+). | >250 | $^1$H-NMR(DMSO-d$_6$) δ (343 K.) = 11.34(s br, 1H); 8.17(d br, 1H); 7.86(d, 1H); 7.77(s, 1H); 7.67(s, 1H); 7.60(d 1H); 7.58(dd, 1H); 7.03(d, 1H); 4.03(s, 3H); 4.03–3.88(m, 1H); 3.17(m, 4H); 2.77–2.50(m, 4H); 1.97(m, 2H); 1.88–1.75(m, 2H); 1.68–1.52(m, 4H). |

TABLE 2

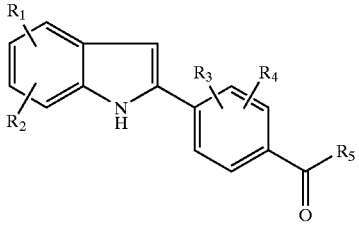

| Ex. | Name | R$_1$ | R$_2$ | R$_3$ | R$_4$ | R$_5$ | MP °C. | N.M.R. |
|---|---|---|---|---|---|---|---|---|
| 17 | 4-(5,6-Dichloro-1H-indol-2-yl)-N-(2,2,6,6-tetramethylpiperidin-4-yl)-3-(hydroxycarbonyl-methoxy)benzamide | 5-Cl | 6-Cl | 3-OCH$_2$COOH | —H | 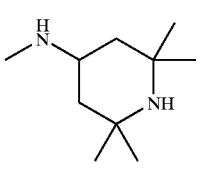 | 260 | $^1$H-NMR(DMSO-d$_6$) = 14.50 (s br, 1H); 8.60(s br, 1H); 8.50 (d, 1H); 7.88(d, 1H); 7.77(s, 1H); 7.60(s, 1H); 7.54(s, 1H); 7.50(d, 1H); 7.00(s, 1H); 4.57 (s, 2H); 4.45(m, 1H); 2.00(d, 2H); 1.68(dd, 2H); 1.40(s, 6H); 1.36(s, 6H). |
| 18 | 4-(5,6-Dichloro-1H-indol-2-yl)-N-(2,2,6,6-tetramethylpiperidin-4-yl)-3-(2-hydroxy-ethoxy)benzamide | 5-Cl | 6-Cl | 3-OCH$_2$CH$_2$OH | —H | 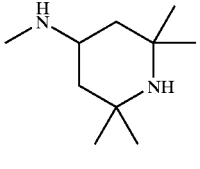 | 270–272 | $^1$H-NMR(DMSO-d$_6$) = 11.65 (s, 1H); 8.22(d, 1H); 7.88(d, 1H); 7.80(s, 1H); 7.60–7.52(m, 3H); 7.15(s, 1H); 5.30(m, 1H); 4.35–4.20(m, 3H); 3.90(m, 2H); 1.70(d, 2H); 1.20(s, 6H); 1.12 (m, 2H); 1.07(s, 6H). |
| 19 | 4-(5,6-Dichloro-1H-indol-2-yl)-N-(2,2,6,6-tetramethylpiperidin-4-yl)-3-(3-amino-propoxy)-benzamide | 5-Cl | 6-Cl | 3-O(CH$_2$)$_3$NH$_2$ | —H | 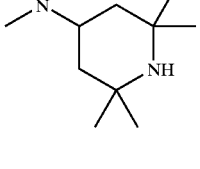 | 194 | $^1$H-NMR(DMSO-d$_6$) = 11.70(s, 1H); 8.23(d, 1H); 7.80–7.75(m, 2H); 7.65–7.50(m, 3H); 7.05(s, 1H); 4.35–4.20(m, 3H); 3.35(m, 2H); 2.00(m, 2H); 1.75–1.60(m, 2H); 1.20(m, 2H); 1.18(s, 6H); 1.05(s, 6H). |
| 20 | 4-(5,6-Dichloro-1H-indol-2-yl)-N-(2,2,6,6-tetramethylpiperidin-4-yl)-3-(2-dimethylamino-ethoxy)benzamide | 5-Cl | 6-Cl | 3-O(CH$_2$)$_2$N(Me)$_2$ | —H | 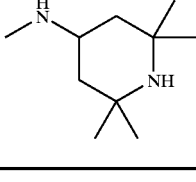 | 263–265 | $^1$H-NMR(DMSO-d$_6$) = 12.25(s, 1H); 8.21(d br, 1H); 7.85(m, 1H); 7.60(s, 1H); 7.80(s, 1H); 7.56–7.49(m, 3H); 7.09(s, 1H); 4.40–4.25(m, 3H); 2.78(m, 2H); 2.35(s, 6H); 1.71(m, 2H); 1.19 (s, 6H); 1.13(m, 2H); 1.06(s, 6H). |
| 21 | 4-(5,6-Dichloro-1H-indol-2-yl)-N-(2,2,6,6-tetramethylpiperidin-4-yl)-3-(2,3-dihydroxy-propoxy)benzamide | 5-Cl | 6-Cl | 3-OCH$_2$CH(OH)CH$_2$OH | —H | | 252 | $^1$H-NMR(DMSO-d$_6$) = 11.75(s br, 1H); 8.34(s br, 1H); 7.90(d, 1H); 7.80(s, 1H); 7.65(s, 1H); 7.60(s, 1H); 7.56(d, 1H); 7.15(s, 1H); 5.50(d, 1H); 5.04(t, 1H); 4.40–4.24(m, 2H); 4.20–4.00 (m, 2H); 1.90–1.75(m, 2H); 1.40–1.10(m, 14H). |

Biological Assays

Background. It is known that, upon attachment to bone, an electrogenic H$^+$-adenosine triphosphatase (ATPase) is polarised to the osteoclast-bone interface. The pump transports massive quantities of protons into the resorption microenvironment to effect mobilisation of the bone mineral and to create the acidic pH required by collagenases to degrade the bone matrix.

The vacuolar nature of the osteoclast proton pump was originally recognised by Blair [H. C. Blair at al., Science, 245, 855 (1989)] and than confirmed by Bekker [P. J. Bekker et al., J. Bone Min. Res., 5, 569 (1990)] and Väänänen [H. K. Väänänen et al., J. Cell. Biol., 111, 1305 (1990)]. Evidence was based upon preparations of ruffled membrane fragments from avian osteoclasts (obtained from the medullar bone of calcium-starved egg-laying hens). The resulting membrane vesicles acidify in response to ATP, which is easily assessed by measuring the fluorescence quench of acridine orange, a weak base which accumulates into acidic compartments.

The biochemical pattern indicated that the osteoclast proton pump belonged to the vacuolar-like ATPases since proton transport was inhibited by N-ethylmaleimide (NEM), a sulphydryl reagent, and by bafilomycin $A_1$, a selective inhibitor of vacuolar $H^+$-ATPases [J. E. Bowman et al., *Proc. Natl. Acad. Sci. USA*, 85, 7972 (1988)], whilst it was not inhibited by ouabain, an inhibitor of $Na^+/K^+$-ATPases; sodium orthovanadate, an inhibitor of P-ATPases, or by omeprazole or SCH 28080, both of which are inhibitors of gastric $H^+/K^+$-ATPase [J. P. Mattsson et al., *Acta Physiol. Scand.*, 146, 253 (1992)].

It is known that specific inhibitors of vacuolar ATPases, such as bafilomycin $A_1$, are able to inhibit bone resorption in osteoclast cultures [K. Sundquist et al., *Biochem. Biophys. Res. Commun.* 168, 309–313 (1990)]

Inhibition of Proton Transport and v-ATPase Activity in Membrane Vesicles

Preparation of Crude Bone Microsomes from Calcium-starved Egg-laying Hens.

Vesicles were prepared from medullar bone obtained from tibiae and femurs of egg-laying hens which were calcium-starved for at least 15 days. Briefly, bone fragments were scraped with a 24 scalpel blade, suspended in 40 ml of isolation medium (0.2 M sucrose, 50 mM KCl, 10 mM Hepes, 1 mM EGTA, 2 mM dithiotheitrol, pH 7.4) and filtered through a 100 μm pore size nylon mesh. The whole procedure was performed at 4° C. After homogenisation in a potter (20 strokes) in 40 ml of isolation medium an initial centrifugation ($6,500 \times g_{max} \times 20$ min) was performed to remove mitochondria and lysosomes. The supernatant was centrifuged at $100,000 \times g_{max}$ for 1 hr and the pellet was collected in 1 ml of isolation medium, divided into 200 μl aliquots, immediately frozen in liquid nitrogen and stored at −80° C. The protein content was determined using a Biorad colourimetric kit according to Bradford [M. Bradford, *Anal. Biochem.* 72, 248 (1976)]. For the proton transport assay, 5–10 μl of membranes were used.

Purification of osteoclast membranes. 1 ml of crude microsomal vesicles prepared above were applied (about 0.2 ml per tube) on the top of a sucrose step-gradient consisting of 3.5 ml of 15%, 30% and 45% (w/w) sucrose in isolation medium and centrifuged at 280,000 $g_{max}$ for 2 h (SW 41 Ti rotor). After centrifugation the 30–45% sucrose interfaces were collected, diluted approx. 20-fold in isolation medium and pelletted at 100,000 $g_{max}$ for 1 hour (SW 28 rotor). The pellet was then resuspended in 1 ml of isolation medium, aliquoted and frozen in liquid $N_2$ and stored at −80° C. until used.

Human kidney membranes were obtained from the cortex of a human kidney, frozen immediately after surgery, according to the method reported in the literature for bovine kidney (S. Gluck, *J. Biol. Chem.*, 265, 21957 (1990)).

Preparation of human osteoclast microsomal vesicles. Osteoclast-like giant cells isolated from osteoclastoma tumor were homogenized with a glass-teflon homogenizer (1000 rpm×20 strokes), and the material was centrifuged at 6000×gmax for 20 minutes. The resulting pellet was then spun at 100000×gmax for 60 minutes to pellet the microsomal fraction. Resuspended in 1 ml of isolation medium pH 7.4, frozen by liquid nitrogen immersion and stored at −80° C. until used.

Proton transport in membrane vesicles was assessed, semi-quantitatively, by measuring the initial slope of fluorescence quench of acridine orange (excitation 490 nm; emission 530 nm) after addition of 5–20 μl of membrane vesicles in 1 ml of buffer containing 0.2 M sucrose, 50 mM KCl, 10 mM Hepes pH 7.4, 1 mM ATP.Na2, 1 mM CDTA, 5 μM valinomycin and 4 μM acridine orange. The reaction was started by addition of 5 mM MgSO4. Results were expressed as the percent of the mean of two controls.

Inhibition of bafilomycin-sensitive ATPase activity was assessed in purified membrane vesicles by measuring the release of inorganic phosphate (Pi) during 30 min of incubation at 37° C. in a 96-well plate either in the presence or in the absence of bafilomycin A1. The reaction medium contained 1 mM ATP, 10 mM HEPES-Tris pH 8, 50 mM KCl, 5 uM valinomycin, 5 uM nigericin, 1 mM CDTA-Tris, 100 uM ammonium molybdate, 0.2 M sucrose and membranes (20 ug protein/ml). The reaction was initiated by $MgSO_4$ (8-arm pipette) and stopped, after 30 min, by addition of 4 volumes of the malachite green reagent (96-arm pipette) prepared according to Chan [*Anal. Biochem.* 157, 375 (1986)]. Absorbance at 650 nm was measured after 2 min using a microplate reader. Results are expressed as nmol (Pi)×mg protein$^{-1}$×min$^{-1}$ and, for each experiment, represent the mean±sem of triplicates.

Pharmacological Data

Compounds described in the present invention are able to inhibit bafilomycin-sensitive ATPase of chicken osteoclast in a range from 50 nM to 2 μM and of human osteoclast in a range from 30 nM to 5 μM.

What is claimed is:

1. A compound of formula (I)

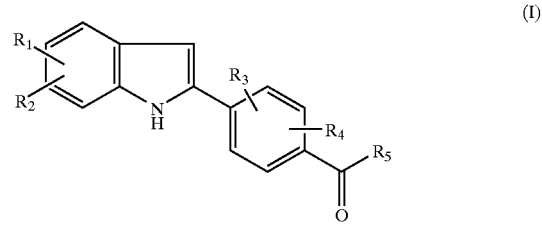

or a salt thereof, or a solvate thereof, wherein;

$R_1$ and $R_2$ each independently represents $C_{1-6}$alkoxy or halo;

$R_3$ and $R_4$ each independently represents hydrogen, $C_{1-6}$alkoxy, aryl$C_{1-6}$alkoxy, hydroxy, carboxy$C_{1-6}$alkoxy, hydroxy$C_{1-6}$alkoxy, dihydroxy$C_{1-6}$alkoxy, mono- and di-($C_{1-6}$alkyl)amino$C_{1-6}$alkoxy or amino $C_{1-6}$alkoxy and;

$R_5$ represents —$NR_sR_t$ wherein $R_s$ and $R_t$ each independently represent hydrogen, unsubstituted or substituted $C_{1-6}$alkyl, or unsubstituted or substituted heterocyclyl.

2. A compound according to claim 1 wherein $R_1$ and $R_2$ each independently represents methoxy or chloro.

3. A compound according to claim 1 wherein $R_1$ is 5-chloro and $R_2$ is 6-chloro.

4. A compound according to claim 1 wherein $R_3$ is hydroxy, methoxy, ethoxy, propoxy, benzyloxy, carboxyethoxy, hydroxyethoxy, dihydoxypropoxy, dimethylaminoethoxy or aminopropoxy.

5. A compound according to claim 1 wherein $R_4$ is hydrogen or methoxy.

6. A compound according to claim 1 wherein $R_s$ or $R_t$ represent unsubstituted or substituted $C_{1-6}$alkyl, or unsubstituted or substituted heterocyclyl.

7. A compound according to claim 1 wherein $R_s$ or $R_t$ represent 3-[4-(3-methoxyphenyl)piperazin-1-yl]propyl or 3-[4-(2-pyrimidinyl)piperazin-1-yl]propyl.

8. A compound according to claim 1 wherein $R_s$ or $R_t$ represent an unsubstituted or substituted piperidinyl group.

9. A compound according to claim 1 wherein $R_s$ or $R_t$ represent a 1,2,2,6,6-pentamethylpiperidin-4-yl group or a 2,2,6,6-tetramethylpiperidin-4-yl group.

10. A compound according to claim 1 wherein $R_t$ is hydrogen.

11. A compound according to claim 1 wherein;

$R_s$ is 3-[4-(3-methoxyphenyl)piperazin-1-yl]propyl or 3-[4-(2-pyrimidinyl)piperazin-1-yl]propyl, and $R_t$ is hydrogen or a salt thereof or a solvate thereof.

12. A compound according to claim 1 wherein;

$R_s$ is 3-pyridyl or 3-(6-methoxy)pyridyl, and $R_t$ is hydrogen or a salt thereof or a solvate thereof.

13. A compound according to claim 1 wherein;

$R_s$ is 2,2,6,6-tetramethylpiperidin-4-yl, $R_t$ is hydrogen, R3 is 3-ethoxy, and $R_1$ is 5-chloro or 5-methoxy or a salt thereof or a solvate thereof.

14. A compound according to claim 1 wherein;

$R_s$ is 2,2,6,6-tetramethylpiperidin-4-yl, $R_t$ is hydrogen, $R_3$ is 2-methoxy, 3-methoxy, 3-ethoxy, 3-propoxy, 3-benzyloxy, 3-(2-carboxyethoxy), 3-(2-hydroxyethoxy), 3-(2,3-dihydroxypropoxy), 3-(2-dimethylaminoethoxy) or 3-(3-aminopropoxy) and 3-hydroxy and $R_4$ is 5-methoxy or hydrogen or a salt thereof or a solvate thereof.

15. A compound according to claim 1 wherein;

$R_s$ is 1,2,2,6,6-pentamethylpiperidin-4-yl, $R_t$ is hydrogen, and $R_3$ is 2-methoxy or 3-ethoxy, and $R_4$ is 5-methoxy or hydrogen or a salt thereof or a solvate thereof.

16. A compound according to claim 1 wherein;

$R_s$ is 1-benzylpiperidin-4-yl, 1-(4-ethoxycarbonyl)butylpiperydin-4-yl, 1-(4-hydroxycarbonyl)butylpiperydin-4-yl and $R_t$ is hydrogen or a salt thereof or a solvate thereof.

17. A compound selected from the list consisting of:

4-(5,6-dichloro-1H-indol-2-yl)-3-ethoxy-N-(2,2,6,6-tetramethylpiperidin-4-yl)-benzamide;

4-(5,6-dichloro-1H-indol-2-yl)-3-benzyloxy-N-(2,2,6,6-tetramethylpiperidin-4-yl)-benzamide;

4-(5,6-dichloro-1H-indol-2-yl)-3-hydroxy-N-(2,2,6,6-tetramethylpiperidin-4-yl)-benzamide;

4-(5,6-dichloro-1H-indol-2-yl)-3-propoxy-N-(2,2,6,6-tetramethylpiperidin-4-yl)benzamide;

4-(5,6-dichloro-1H-indol-2-yl)-N-[3-[4-(3-methoxyphenyl)piperazin-1-yl]propyl]-3-methoxybenzamide;

4-(5,6-dichloro-1H-indol-2-yl)-N-[3-[4-(2-pyrimidyl)piperazin-1-yl]propyl]-3-methoxybenzamide;

4-(5,6-dichloro-1H-indol-2-yl)-N-(2,2,6,6-tetramethylpiperidin-4-yl)-3-methoxybenzamide;

4-(5,6-dichloro-1H-indol-2-yl)-N-(1,2,2,6,6-pentamethylpiperidin-4-yl)-3-ethoxybenzamide;

4-(5,6-dichloro-1H-indol-2-yl)-N-(3-pyridyl)-3-ethoxybenzamide;

4-(5,6-dichloro-1H-indol-2-yl)-N-(3-(6-methoxypyridyl))-3-ethoxybenzamide;

4-(5,6-dichloro-1H-indol-2-yl)-N-(1-benzylpiperidin-4-yl)-3-ethoxybenzamide;

4-(5,6-dichloro-1H-indol-2-yl)-N-(2,2,6,6-tetramethylpiperidin-4-yl)-2,5-dimethoxybenzamide;

4-(5,6-dichloro-1H-indol-2-yl)-N-(1,2,2,6,6-pentamethylpiperidin-4-yl)-2,5-dimethoxybenzamide;

4-(5-methoxy-6-chloro-1H-indol-2-yl)-N-(2,2,6,6-tetramethylpiperidin-4-yl)-3-ethoxybenzamide;

4-(5,6-dichloro-1H-indol-2-yl)-3-methoxy-N-((1-ethoxycarbonylpentyl)piperidin-4-yl)-benzamide;

4-(5,6-dichloro-1H-indol-2-yl)-3-methoxy-N-((carboxybutyl)piperidin-4-yl)benzamide;

4-(5,6-dichloro-1H-indol-2-yl)-N-(2,2,6,6-tetramethylpiperidin-4-yl)-3-(hydroxycarbonylmethoxy)benzamide;

4-(5,6-dichloro-1H-indol-2-yl)-N-(2,2,6,6-tetramethylpiperidin-4-yl)-3-(2-hydroxy-ethoxy)benzamide;

4-(5,6-dichloro-1H-indol-2-yl)-N-(2,2,6,6-tetramethylpiperidin-4-yl)-3-(3-amino-propoxy)benzamide;

4-(5,6-dichloro-1H-indol-2-yl)-N-(2,2,6,6-tetramethylpiperidin-4-yl)-3-(2-dimethylaminoethoxy)benzamide, and;

4-(5,6-dichloro-1H-indol-2-yl)-N-(2,2,6,6-tetramethylpiperidin-4-yl)-3-(2,3-hydroxy-propoxy)benzamide.

18. A process for the preparation of a compound of formula (I) as defined in claim 1 or a salt thereof or a solvate thereof, which process comprises the amidation of a compound of formula (II)

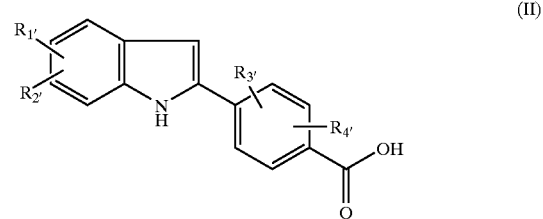

(II)

wherein;

$R_{1'}$, $R_{2'}$, $R_{3'}$, and $R_{4'}$ each respectively represent $R_1$, $R_2$, $R_3$, and $R_4$ as defined in relation to formula (I) or a protected from thereof, with a compound of formula (III)

(III)

wherein;

$R_{s'}$ and $R_{t'}$ each represent $R_s$ and $R_t$ as defined in relation to formula (I) or a protected from thereof and thereafter, as necessary, carrying out one or more of the following steps:

(i) converting one compound of formula (I) into another compound of formula (I);

(ii) removing any protecting group;

(iii) preparing a salt or solvate of the compound so formed.

19. A method for the treatment and/or prophylaxis of diseases associated with over activity of osteoclasts in mammals which method comprises the administration of an effective non-toxic amount of a compound of formula (I) as defined in claim 1, or a pharmaceutically acceptable salt thereof, or a pharmaceutically acceptable solvate thereof.

20. A method for the treatment of osteoporosis and related osteopenic diseases in a human or non-human mammal, which comprises administering an effective, non-toxic, amount of a compound of formula (I) as defined in claim 1 or a pharmaceutically acceptable salt thereof or a pharmaceutically acceptable solvate thereof, to a human or non-human mammal in need thereof.

21. A method for the treatment of ulcers, hypercholesterolemic and atherosclerotic diseases, AIDS, and angiogenic diseases, in a human or non-human mammal, which comprises administering an effective, non-toxic, amount of a compound of formula I according to claim 1 or a pharmaceutically acceptable salt thereof or a pharmaceutically acceptable solvate thereof, to a human or non-human mammal in need thereof.

22. A pharmaceutical composition comprising a compound of formula as defined in claim 1 or a pharmaceutically acceptable salt thereof or a pharmaceutically acceptable solvate thereof and a pharmaceutically acceptable carrier therefor.

* * * * *